US009139696B1

(12) United States Patent
Tan et al.

(10) Patent No.: US 9,139,696 B1
(45) Date of Patent: Sep. 22, 2015

(54) AROMATIC DIAMINES CONTAINING THREE ETHER-LINKED-BENZONITRILE MOIETIES, POLYMERS THEREOF, AND METHODS OF MAKING THE SAME

(71) Applicant: The United States of America, as represented by the Secretary of the Air Force, Washington, DC (US)

(72) Inventors: Loon-Seng Tan, Centerville, OH (US); David Huabin Wang, Beavercreek, OH (US)

(73) Assignee: The United States of America, as represented by the Secretary of the Air Force, Washington, DC (US)

( * ) Notice: Subject to any disclaimer, the term of this patent is extended or adjusted under 35 U.S.C. 154(b) by 0 days.

(21) Appl. No.: 14/229,251

(22) Filed: Mar. 28, 2014

(51) Int. Cl.
| C08G 73/00 | (2006.01) |
| C08G 73/10 | (2006.01) |
| C07C 255/54 | (2006.01) |
| C07C 253/30 | (2006.01) |
| C07C 231/06 | (2006.01) |
| C08G 73/14 | (2006.01) |

(52) U.S. Cl.
CPC .......... *C08G 73/1071* (2013.01); *C07C 231/06* (2013.01); *C07C 253/30* (2013.01); *C07C 255/54* (2013.01); *C08G 73/14* (2013.01); *Y10S 430/107* (2013.01)

(58) Field of Classification Search
CPC .... C07C 253/30; C07C 231/06; C08G 73/14; Y10S 430/107
USPC .......................................... 528/170, 310, 353
See application file for complete search history.

(56) References Cited

U.S. PATENT DOCUMENTS

| 3,455,879 A | 7/1969 | Gay et al. |
| 3,514,415 A | 5/1970 | Karol |
| 3,600,361 A | 8/1971 | Heacock et al. |
| 3,732,200 A | 5/1973 | Bach |
| 3,763,211 A | 10/1973 | Heath et al. |
| 3,835,120 A | 9/1974 | Bach et al. |
| 3,925,312 A | 12/1975 | Fletcher |
| 3,988,374 A | 10/1976 | Brode et al. |
| 4,107,125 A | 8/1978 | Lovejoy |
| 4,111,906 A | 9/1978 | Jones et al. |
| 4,203,922 A | 5/1980 | Jones et al. |
| 4,271,288 A | 6/1981 | Woo |
| RE30,922 E | 5/1982 | Hellman et al. |
| 4,394,499 A | 7/1983 | Robinson |
| 4,535,101 A | 8/1985 | Lee et al. |
| 4,728,697 A | 3/1988 | Bolon et al. |
| 4,797,466 A | 1/1989 | Oikawa et al. |
| 4,981,497 A | 1/1991 | Hayes |
| 5,101,005 A | 3/1992 | Vora et al. |
| 5,101,037 A | 3/1992 | McGrath et al. |
| 5,175,234 A | 12/1992 | Lubowitz et al. |
| 5,205,894 A | 4/1993 | Ohta et al. |
| 5,278,276 A | 1/1994 | Ohta et al. |
| 5,300,559 A | 4/1994 | Sheehan et al. |
| 5,344,894 A | 9/1994 | Lubowitz et al. |
| 5,411,765 A | 5/1995 | Kanakarajan et al. |
| 5,508,377 A | 4/1996 | Yamashita et al. |
| 5,516,876 A | 5/1996 | Lubowitz et al. |
| 5,585,217 A | 12/1996 | Oba |
| 5,599,582 A | 2/1997 | Adamopoulos et al. |
| 5,610,265 A | 3/1997 | Tan |
| 5,631,377 A | 5/1997 | Matsuo et al. |
| 5,670,651 A | 9/1997 | Tan et al. |
| 5,705,574 A | 1/1998 | Lubowitz et al. |
| 5,891,581 A | 4/1999 | Simpson et al. |
| 5,965,687 A | 10/1999 | Jensen |
| 6,001,277 A | 12/1999 | Ichimura et al. |
| 6,184,333 B1 | 2/2001 | Gray |
| 6,262,223 B1 | 7/2001 | Meador et al. |
| 6,307,008 B1 | 10/2001 | Lee et al. |
| 6,379,809 B1 | 4/2002 | Simpson et al. |
| 6,509,094 B1 | 1/2003 | Shah et al. |
| 7,402,264 B2 | 7/2008 | Ounaies et al. |
| 7,507,472 B2 | 3/2009 | Ounaies et al. |

(Continued)

FOREIGN PATENT DOCUMENTS

| EP | 19900108350 | 11/1990 |
| EP | 2380867 | 10/2011 |

(Continued)

OTHER PUBLICATIONS

Klein et al (Synthesis and Characterization of Polyimides Derived From Cyano-Containing 1,4-Bis(4-aminophenoxy)benzene Monomers, Polymer Bulletin 59, 1-12 (2007), Jan. 2007.*
USPTO structure search, Jul. 2015.*
Liaw, D-J, et al., "High Glass Transitions of New Polyamides, Polyimides, and Poly(amide-imide)s Containing a Triphenylamine Group: Synthesis and Characterization," Macromolecules, 2002, 35 (12), pp. 4669-4676.
Wang, D.H., et al., "High-Temperature Dielectric Polyimide Films for Energy Storage Applications," MRS Online Proceedings Library, vol. 1541, Jan. 2013, Published online by Cambridge University Press: Jun. 6, 2013.
Klein, D.J., et al., "Synthesis and Characterization of Polyimides Derived From Cyano-Containing 1,4-Bis(4-aminophenoxy)benzene Monomers," Polymer Bulletin, vol. 59 (1) Jun. 1, 2007, pp. 1-12.
Hamciuc, E., et al., "Aromatic Polyimides Containing Polar Nitrile Groups," Revue Roumaine de Chimie, 2006, 51(7-8), 765-771.
Mercer, F.W., et al., "Synthesis and properties of new alternating copolyethers containing pendent cyano groups," Polymer, vol. 34 (24) Nov. 1994, 5355-5363.

(Continued)

*Primary Examiner* — Gregory Listvoyb
(74) *Attorney, Agent, or Firm* — AFMCLO/JAZ; James P. Carey

(57) ABSTRACT

The present invention includes compositions and methods of preparation for symmetrical and unsymmetrical diamines containing three ether-linked benzonitrile moieties that may be used as monomers for the manufacture of a variety of functional polymers. For example, the presently disclosed multi(ether-benzonitrile) diamines may polymerize with: (i) a dianhydride to form a polyimide; (ii) a diacid chloride directly or with a dicarboxylic acid (diacid) in conjunction with a suitable promoter/catalyst combination such as triethylphosphite/pyridine to form a polyamide; and (iii) 1,2,4-benzenetricarboxylic anhydride (trimellitic anhydride), trimellitic anhydride chloride, or a diacid/diacid chloride derived from trimellitic anhydride and an aromatic diamine to form a poly(amide-imide).

15 Claims, 5 Drawing Sheets

(56) References Cited

U.S. PATENT DOCUMENTS

| | | | |
|---|---|---|---|
| 7,527,751 | B2 | 5/2009 | Ounaies et al. |
| 7,582,722 | B1 | 9/2009 | Tan et al. |
| 7,588,699 | B2 | 9/2009 | Park et al. |
| 7,678,873 | B1 | 3/2010 | Tan et al. |
| 7,906,043 | B2 | 3/2011 | Connell et al. |
| 7,935,414 | B2 | 5/2011 | Ounaies et al. |
| 7,972,536 | B2 | 7/2011 | Connell et al. |
| 8,034,893 | B2 | 10/2011 | Akiba et al. |
| 8,173,763 | B1 | 5/2012 | Tan et al. |
| 8,314,203 | B2 | 11/2012 | Tsutsumi et al. |
| 8,389,619 | B1 | 3/2013 | Tan et al. |
| 8,546,614 | B1 | 10/2013 | Tan et al. |
| 8,633,284 | B2 | 1/2014 | Ronk et al. |
| 8,785,589 | B1 | 7/2014 | Tan et al. |
| 8,791,227 | B1 | 7/2014 | Tan et al. |
| 2003/0064235 | A1 | 4/2003 | Okawa et al. |
| 2004/0233377 | A1 | 11/2004 | Utsumi et al. |
| 2005/0080229 | A1 | 4/2005 | Deets et al. |
| 2006/0057377 | A1 | 3/2006 | Harrison et al. |
| 2006/0217482 | A1 | 9/2006 | Lukehart et al. |
| 2006/0235194 | A1 | 10/2006 | Kato |
| 2006/0270825 | A1 | 11/2006 | Angermeier et al. |
| 2007/0106056 | A1 | 5/2007 | Itatani |
| 2007/0270562 | A1 | 11/2007 | Yamada et al. |
| 2007/0272124 | A1 | 11/2007 | Tsutsumi et al. |
| 2008/0025905 | A1 | 1/2008 | Wang et al. |
| 2008/0311303 | A1 | 12/2008 | Naiki et al. |
| 2009/0220722 | A1 | 9/2009 | Wang |
| 2010/0048745 | A1 | 2/2010 | Yamada et al. |
| 2011/0009513 | A1 | 1/2011 | Chaudhary et al. |
| 2011/0136061 | A1 | 6/2011 | Itatani |

FOREIGN PATENT DOCUMENTS

| | | |
|---|---|---|
| GB | 1147856 | 4/1969 |
| JP | EP19890302445 | 3/1989 |
| JP | EP19870301063 | 12/1993 |
| JP | EP19940309548 | 6/1995 |
| JP | EP19940309548 | 3/1999 |
| JP | 2005023151 | 1/2005 |
| JP | 2005154643 | 6/2005 |
| WO | PCTJP2004019528 | 4/2006 |
| WO | PCTES2008000514 | 4/2010 |

OTHER PUBLICATIONS

Gonzalo, B., et al., "Synthesis, Characterization, and Thermal Properties of Piezoelectric Polyimides," Journal of Polymer Science: Part A: Polymer Chemistry, vol. 47, 722-730 (2009).

Liaw, D-J, et al., "Novel Organosoluble Poly(pyridine-imide) with Pendent Pyrene Group: Synthesis, Thermal, Optical, Electrochemical, Electrochromic, and Protonation Characterization," Macromolecules, 2007, 40 (10), pp. 3568-3574.

Liaw, D-J, et al., "Novel poly(pyridine imide) with pendent naphthalene groups: Synthesis and thermal, optical, electrochemical, electrochromic, and protonation characterization," Journal of Polymer Science Part A: Polymer Chemistry vol. 45, Issue 12, pp. 2367-2374, Jun. 15, 2007.

Hamciuc, E., et al., "Study of thin films made from poly (amide-imide)s containing nitrile groups," 2010 International Semiconductor Conference (CAS), Oct. 11-13, 2010 (vol. 02), 341-344.

Kang, H.A., et al., "Synthesis and Characterization of Polyimides from Unsymmetrical Diamine with Cyano Groups," Polymer Journal (2001) 33, 284-289.

Saxena, A., et al., "Synthesis and characterization of polyamides and poly(amide-imide)s derived from 2,6-bis(3-aminophenoxy)benzonitrile or 2,6-bis(4-aminophenoxy)benzonitrile," Polymer International, vol. 54, Issue 3, pp. 544-552, Mar. 2005.

Ounaies, Z., et al., "Structure-property study of piezoelectricity in polyimides," Smart Structures and Materials 1999: Electroactive Polymer Actuators and Devices, Newport Beach, CA, Mar. 1, 1999, Y. Bar-Cohen, ed., Proc. SPIE 3669, pp. 171-178.

Wang, D.H., et al., "Synthesis of Symmetric and Asymmetric Polyimides Containing Benzonitrile Groups for Dielectric Applications," Polymer Preprints 2010, 51(2),522-533.

Jacobs, J.D., et al., "Dielectric characteristics of polyimide CP2," Polymer, vol. 51, Issue 14, Jun. 24, 2010, pp. 3139-3146.

Young, J.A., et al., "Molecular modeling of the poling of piezoelectric polyimides," Polymer, vol. 40, Issue 10, May 1999, pp. 2787-2795.

Park, C., et al., "In situ poling and imidization of amorphous piezoelectric polyimides," Polymer, vol. 45, Issue 16, Jul. 21, 2004, pp. 5417-5425.

Wang, D.H., et al., "Synthesis and Characterization of Unsymmetrical Benzonitrile-Containing Polyimides: Viscosity-Lowering Effect and Dielectric Properties," Journal of Polymer Science, Part A: Polymer Chemistry 2013, 51, 4998-5011.

Li, L. et al., "Synthesis and Characterization of New Polyimides Containing Nitrile Groups," High Performance Polymers, Mar. 2005, 17(1):135-147.

Amaranatha Reddy, R., et al., "Occurrence of the B 7 mesophase in two homologous series of seven-ring achiral compounds composed of banana-shaped molecules," Liquid Crystals, vol. 30, Issue 3, 2003, pp. 273-283.

Hamciuc, E., et al., "Hybrid Films Based on a Polyimide Containing Nitrile Groups and Barium and Titanium Oxides," High Performance Polymers, Jan. 2010, 22(2):225-236.

Hamciuc, C., et al., "Aromatic Poly(ether imide)s Containing Nitrile Groups," High Performance Polymers, Jan. 2009; 21(2):205-218.

Koton, M.M., et al., "Polyimides containing different heterocyclic units in the main chain," Chemical Abstracts, vol. 96, No. 4, Jan. 25, 1982, p. 5, col. 1, abstract No. 20532k, Columbus, Ohio.

Koton, M.M., et al., "Polyimides containing various heterocyclic main-chain units," Polymer Science U.S.S.R., vol. 23, Issue 8, 1981, pp. 1909-1915.

Agolini et al., "Synthesis and properties of azoaromatic polymers," Macromol., vol. 3 (1970) 349-351.

Arlen et al., "Thermal-electrical character of in situ synthesized polyimide-grafted carbon nanofiber composites," Macromol., vol. 41 (2008) 8053-8062.

Barrett et al., "Photo-mechanical effects in azobenzene-containing soft materials," J. Soft Mater., vol. 3 (2007) 1249-1261.

Behl et al., "Shape-memory polymers," Mater. Today, vol. 10 (2007) 20-28.

Chao et al., "Nonlinear optical polyimide/montmorillonite nanocomposites consisting of azobenzene dyes," Dyes and Pigments, vol. 77 (2008) 515-524.

Chen et al., "Highly stable optically induced birefringence and holographic surface gratings on a new azocarbazole-based polyimide," Macromol., vol. 32 (1995) 8572-8579.

Cojocariu et al., "Light-induced motions in azobenzene-containing polymers," Pure Appl. Chem., vol. 76 (2004) 1479-197.

Eisenbach et al., "Isomerization of aromatic azo chromophores in poly(ethyl acrylate) networks and photomechanical effect," Polymer, vol. 21 (1980) 1175-1179.

Fay et al., "Molecularly oriented polymeric thin film for space applications," High Perf. Polym., vol. 11 (1999) 145-156.

Finkelmann et al., "A new opto-mechanical effect in solids," Phys. Rev. Lett., vol. 87 (2001) 015501111-01550114.

Georgiev et al., "Polyimide coatings containing azo-chromophores as structural units," J. Physics Conf. Ser., vol. 113 (2008) 012032.

Harris et al., "Large amplitude light-induced motion in high elastic modulus polymer actuators," J. Mater. Chem., vol. 15 (2005) 5043-5048.

He et al., "Degenerate two-photon-absorption spectral studies of highly two-photon active organic chromophores," J. Chem. Phys., vol. 120 (2004) 5275-5284.

Hergenrother, "Recent Developments in High Temperature Organic Polymers," Polyimides and Other High-Temperature Polymers, Abadie, M.J.M. and Sillion, B., Eds., Elsevier: New York, 1991, pp. 1-18.

Hogan et al., "UV-manipulation of order and macroscopic shape in newmatic elastomers," Phys. Rev. E. Stat. Nonlinear. Sof. Mater. Phys., vol. 65 (2008) 041720001-041720110.

(56) References Cited

OTHER PUBLICATIONS

Hosono et al., "Photochemical control of network structure in gels and photo-induced changes in their viscoelastic properties," Colloids Surf. B: Bioint., vol. 56 (2007) 285-289.

Hrozhyk et al., "Bidirectional photoresponse of surface pretreated azobenzene liquid crystal polymer networks," Optics Express, vol. 17 (2009) 716-722.

Hugel et al., "Single-molecule optomechanical cycle," Science, vol. 496 (2002) 1103-1106.

Irie, "Photochromism and molecular mechanical devices," Bull. Chem. Soc. Japan, vol. 81 (2008) 917-926.

Jenekhe et al., "Nonlinear optical properties of poly(p-phenylenebenzoisoxazole)," Chem. Mater., vol. 4 (1992) 683-687.

Jeong et al., "Adhesion property of novel polyimides containing fluorine and phosphine oxide moieties," J. Adh. Sci. Technol., vol. 15 (2001) 1787-1803.

Kannan et al., "Diphenylaminofluorene-based two-photon-absorbing chormophores with various pi-electron acceptors," Chem. Mater., vol. 13 (2001) 1896-1904.

Kannan et al., "Toward highly active two-photon absorbing liquids. Synthesis and Characterization of 1,3,5-Triazine-based octupolar molecules," Chem. Mater., vol. 16 (2004) 185-14.

Koerner et al., "Polymer design for high temperature shape memory: low crosslink density polyimides," Polymer, vol. 54 (2013) 391-402.

Koerner et al., "Photogenerating work from polymers," Mater. Today, vol. 11 (2008) 34-42.

Kondo et al., "Effect of concentration of photoactive chromophores on photomechanical properties of crosslinked azobenzene liquid-crystalline polymers," J. Mater. Chem., vol. 20 (2010) 117-122.

Koshiba et al, "Photo-induced alignment behavior of azobenzene compound in thin film," Thin Solid Films, vol. 518 (2009) 805-809.

Kumar et al., "Photochemistry of azobenzene-containing polymers," Chem. Rev., vol. 89 (1989) 1915-1925.

Lee et al., "Enhancement of photogenerated mechanical force in azobenzene-functionalized polyimides," Angew. Chem., vol. 124 (2012) 4193-4197.

Lee et al., "Photomechanical response of composite structures built from azobenzene liquid crystal polymer networks," Polymers, vol. 3 (2011) 1447-1457.

Lee et al., "Relationship between the photomechanical response and the thermomechanical properties of azobenzene liquid crystalline polymer networks," Macromol., vol. 43 (2010) 8185-8190.

Lendlein et al., "Shape-memory polymers," Ang. Chem. Int'l. Ed., vol. 41 (2002) 2034-2057.

Li et al., "Light-driven side-on nematic elastomer actuators," Adv. Mater., vol. 15 (2003) 568-572.

Liu et al., "Review of progress in shape-memory polymers," J. Mater. Chem., vol. 17 (2007) 1543-1558.

Lovrein, "The photoviscosity effect," PNAS, vol. 57 (1967) 236-242.

Machine, Translation of WO 2009/013376 as provided by WIPO Patentscope, Powered by Google Translate, accessed on Sep. 30, 2014.

Machine, Translation of JP 2005-023151 as provided by Patent Abstracts of Japan, accessed on Oct. 6, 2014.

Machine, Translation of JP 2005-154643 as provided by Patent Abstracts of Japan, accessed on Sep. 10, 2013.

Makita et al., "Synthesis of alkaline-developable, photosensitive hyperbranced polyimides through the reaction of carboxylic acid dianhydrides and trisamines," J. Polym. Sci. Part A: Polym. Chem., vol. 42 (2004) 3697-3707.

Meador et al., "Improvements to the synthesis of polyimide aerogels," ACS spring Meeting (2011) 34 pages total.

Meador et al., "Synthesis and properties of nanoporous polyimide aerogels having a covalent bonded network structure," Polym. PrePrints, vol. 51 (2010) 265-266.

Miner et al., "The wettability of LaRC colorless polyimide resins on casting surfaces," J. Polym. Mater. Sci. Eng., vol. 76 (1997) 381-382.

Natansohn et al., "Photoinduced motions in azo-containing polymers," Chem. Rev., vol. 201 (2002) 4139-4175.

Park et al., "Actuating single wall carbon nanotube-polymer composites: intrinsic unimorphs," Adv. Mater., vol. 20 (2008) 2074-2079.

Pyun et al., "Kinetics and mechanisms for thermal imidization of a polyamic acid studied by ultraviolet-visible spectroscopy," Macromol., vol. 22 (1989) 1174-1183.

Rabani et al., "Synthesis and characterization of two shape-memory polymers containing short aramid hard segments and poly(e-caprolactone) soft segments," Polymer, vol. 47 (2006) 4251-4260.

Sakamoto et al., "Highly polarized polymer-based light-emitting diodes fabricated by using very thin photoaligned polyimide layers," J. Appl. Phys., vol. 107 (2010) 113108.

Sakamoto et al., "Light exposure dependence of molecular orientation of glassy polyfluorene layers formed on photo-aligned polyimide films," Colloids Surf. B: Bioint., vol. 56 (2007) 260-264.

Schuh et al., "Shape-memory properties of segmented polymers containing aramid hard segments and polycaprolactone soft segments," Polymers, vol. 2 (2010) 71-85.

Serak et al., "Azobenzene liquid crystal polymer-based membrane and cantilever optical systems," Optics Express, vol. 17 (2009) 15736-15746.

Shumaker et la., "Synthesis of high temperature polyaspartimide-urea based shape memory polymers," Polymer, vol. 53 (2012) 4637-4642.

Sinou et al., "Synthesis of a family of triarylphosphanes with fluorous phase affinity," Eur. J. Org. Chem., vol. (2002) 269-275.

Sroog et al., "Polyimides," Prog. Polym. Sci., vol. 16 (1991) 561-594.

SRS Technologies, "Polyimide," Polyimide Films p. 65, Aug. 20, 2004.

St. Clair et al., "Synthesis and characterization of essentially colorless polyimide films," J. Polym. Mater. Sci. Eng., vol. 51 (1984) 62-66.

Straub et al., "Lewis structures of boron compounds involving multiple bonding," J. Chem. Ed., vol. 72 (1995) 494-497.

Tabiryan et al., "Polymer film with optically controlled form and actuation," T. Opt. Exp., vol. 13 (2005) 7442-7448.

Tan et al., U.S. Appl. No. 13/886,524, filed Apr. 19, 2013.

Tyan et al., "Effect of reactivity of organics-modified montmorillonite on the thermal and mechanical properties of montmorillonite/polyimide nanocomposites," Chem. Mater., vol. 13 (2001) 222-226.

Usami et al., "Improvements in photo-alignment efficiency of azobenzene-containing polyimide films," Thin Solid Films, vol. 518 (2009) 729-734.

Usami et al., "Pretilt angle control of liquid crystal molecules by photoaligned films of azobenzene-containing polyimide with a different content of side-chain," J. Appl. Phys., vol. 104 (2008) 113528.

Usami et al., "Photo-aligned blend films of azobenzene-containing polyimides with and without side-chains for inducing inclined alignment of liquid crystal molecules," J. Appl. Phys., vol. 110 (2011) 043522/1-043522/6.

United States Patent and Trademark Office, Non-Final Office Action in U.S. Appl. No. 13/661,194, mailed Jul. 2, 2014, 7 pages total.

United States Patent and Trademark Office, Non-Final Office Action in U.S. Appl. No. 14/013,090, mailed Aug. 22, 2014, 9 pages total.

United States Patent and Trademark Office, Non-Final Office Action in U.S. Appl. No. 13/866,551, mailed Feb. 10, 2014, 6 pages total.

United States Patent and Trademark Office, Non-Final Office Action in U.S. Appl. No. 13/557,326, mailed Sep. 26, 2012, 9 pages total.

United States Patent and Trademark Office Non-Final Office Action in U.S. Appl. No. 13/557,326, mail Mar. 27, 2013, 5 pages total.

United States Patent and Trademark Office Non-Final Office Action in U.S. Appl. No. 13/546,439, mailed Nov. 7, 2013, 9 pages total.

Van Oosten et al., "Bending dynamics and directionality reversal in liquid crystal network photoactuators," Macromol., vol. 41 (2008) 8592-8596.

Van Oosten et al., "Glassy photomechanical liquid-crystal network actuators for microscale devices," Eur. Phys. J. E., vol. 23 (2007) 329-336.

Viswanathan et al., "Surface relief structures on azo polymer films," J. Mater. Chem., vol. 9 (1999) 1941-1955.

Wang et al., "Photomechanical response of glassy azobenzene polyimide networks," Macromol., vol. 44 (2011) 3840-3846.

(56) References Cited

OTHER PUBLICATIONS

Wang et al., "Nanocomposites derived from a low-color aromatic polyimide (CP2) and amine-functionalized vapor-growth carbon nanofibers: in situ polymerization and characterization," Macromol., vol. 40 (2007) 6100-6111.

Whitaker et al., "Synthesis and solid-state structure of substituted arylphosphine oxides," J. Org. Chem., vol. 60 (1995) 3499-3508.

White et al., "A high frequency photodriven polymer oscillator," J. Soft Mater., vol. 4 (2008) 1796-1798.

White et al., "Polarization-controlled, photodriven bending in monodomain liquid crystal elastomer cantilevers," J. Mater. Chem., vol. 19 (2009) 1080-1085.

Xie "Recent advances in polymer shape memory," Polymer, vol. 52 (2011) 4985-5000.

Yu et al., "Photomechanical effects of ferroelectric liquid-crystalline elastomers containing azobenzene chromophores," Angew. Chem. Int'l. Ed., vol. 46 (2007) 881-883.

Yu et al., "Effect of cross-linking density of photoinduced bending behavior of oriented liquid-crystalline network films containing azobenzene," Chem. Mater., vol. 16 (2004) 1637-1643.

Zhang et al., "Rapid bending of a nonliquid crystal azobenzene polymer film and characteristics of surface relief grating," J. Appl. Polym. Sci., vol. 113 (2009) 1330-1334.

United States Patent and Trademark Office, Final Office Action in U.S. Appl. No. 13/661,194, mailed Dec. 11, 2014, 6 pages total.

* cited by examiner

AROMATIC DIAMINES CONTAINING THREE ETHER-LINKED-BENZONITRILE MOIETIES, POLYMERS THEREOF, AND METHODS OF MAKING THE SAME

RIGHTS OF THE GOVERNMENT

The invention described herein may be manufactured and used by or for the Government of the United States for all governmental purposes without the payment of any royalty.

BACKGROUND OF THE INVENTION

1. Field of the Invention

This invention relates generally to the field of heat-resistant polymers with dielectric properties. More particularly, it relates to diamines and polymers containing three ether-linked benzonitrile moieties, polymers made therefrom, and methods of making the same.

2. Description of the Related Art

Materials with a high dielectric constant or relative permittivity (K) have recently received increasing interest for various potential applications including high energy-density-storage capacitor, gate dielectrics, and electroactive materials. In particular, materials with a high dielectric constant and low dielectric loss are critical for the applications of embedded passives such as capacitors. Such materials are one of the enabling technologies for microelectronic-system integration to provide the necessary size reduction without compromising the performance, and in some cases, with the possibility of performance enhancement in electronic systems. For capacitor applications, materials should generally possess the following properties: high dielectric constant, low dissipation factor, high thermal stability, simple processability, and good dielectric properties over a broad frequency range.

However, it is has also become clear that no single material would be able to satisfy all of these prerequisites. Therefore, recent years have witnessed an extensive exploitation of polymer-nanocomposites strategy. The overarching goal of these efforts is to combine the best characteristics of nano-fillers and matrix polymers in a synergistic fashion to improve the dielectric performance of the materials in terms of maximizing the dielectric constant and at the same time, managing the dielectric loss to an acceptable level. From the materials standpoint, there is clearly an increasing need for high-K, non-conducting polymers (i.e. devoid of both intrinsically electronic and ionic conduction) that are processable and compatible with high-K nanoparticles.

With the exception of ferroelectric polymers such as poly(vinylidene fluoride, PVDF (K-values of 9-10) and poly(vinylidene-fluoride-trifluoroethylene) or P(VDF-TrFE)-based, high-K fluoroterpolymers (K>60), the dielectric constant values for organic and nonferroelectric polymers are typically in the 2-4 range. However, the low surface energy of these highly fluorinated polymers makes them poor matrix materials for both carbon-based and inorganic nano-fillers because of the inherent interfacial incompatibility between them. In addition, the useful dielectric properties of these highly fluorinated polymers are generally stable only at temperatures below 125° C.

To increase the dielectric constant property of polymers, one approach that has been explored is to raise the polarity of the molecular chain by introducing highly neutral or zwitterionic polar groups into the side chains. Thus, for flexible aliphatic polymers, namely poly(olefins) and polysiloxanes, highly polar pendants such as cyclic sulfoxide and carbonate, as well as zwitterionic moieties such as pyridium-propanesulfonate and imidazolium-propanesulfonate, have been attached to polymer backbones. The dielectric properties were improved but generally with limited success. For example, cyclic carbonate-containing PMMA appeared to have the best performance: 6.0 (1 KHz), 5.0 (1 MHz), and 3.4 (1 GHz) with dielectric loss of 0.1-0.2 in the testing range of 1 MHz-1 GHz, where the relatively large loss is ascribed to the association of the zwitterionic units under the influence of electric field.

In the case of less flexible, aromatic polyimides, hole-transporting triphenylamine units have been incorporated into the polymer backbone, resulting in dielectric constants (3.57-4.93 at 1 kHz) higher than those of common polyimides (e.g. Kapton® film, DuPont™, with a value of 3.2). Similarly, the aryl-substituted pyridine heterocylic ring and nitrile (—CN) group were found to be effective in raising the K value up to 4.5 at 1 KHz. While no dielectric loss data is reported for these polymers, substantial dielectric loss has been reported for (βCN)APB-ODA, a non-fluorinated polyimide, at temperatures around 150° C. Therefore, mechanically and thermally robust polymer dielectrics are needed to increase the operating temperature range and to mitigate thermal management issues in compact pulsed power applications.

SUMMARY OF THE INVENTION

The present invention includes tri(benzonitrile)-diamines having a general structure:

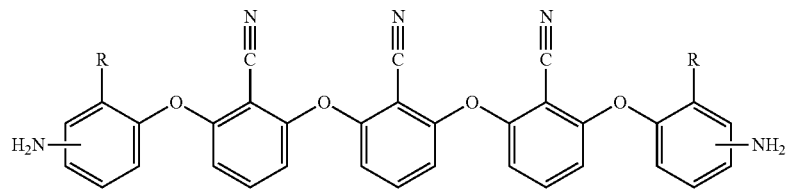

in which NH$_2$ is meta or para with reference to oxygen and R is selected from the group consisting of H, CH$_3$, Cl, F, and CF$_3$. The resulting diamines may be useful as monomers for synthesis of a variety of functional polymers The present invention further includes polyimides derived from the polymerization of the tri(benzonitrile)-diamine and a dianhydride. The polyimide has the general structure:

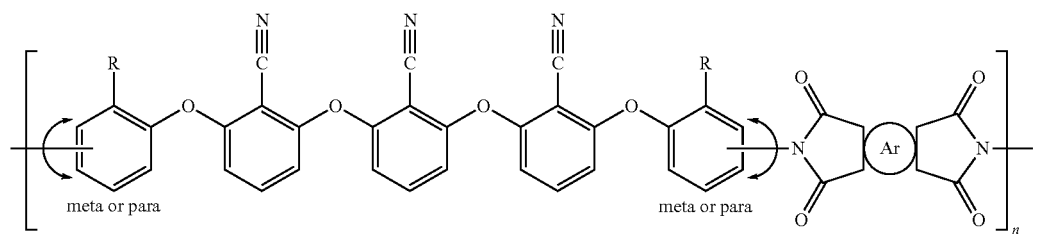

Ar is selected from the group consisting of:

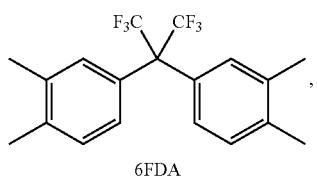
6FDA

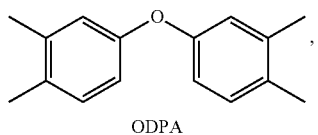
ODPA

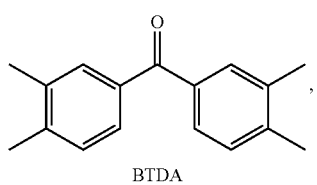
BTDA

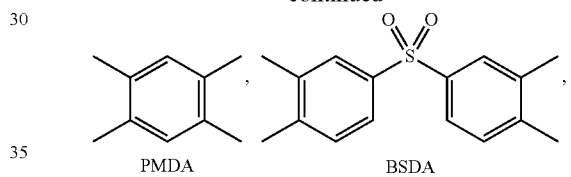
PMDA          BSDA

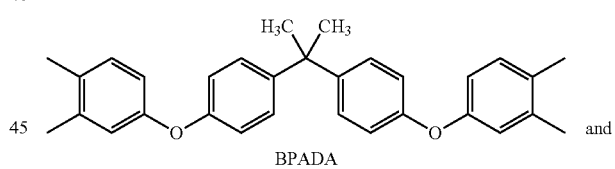
BPADA  and

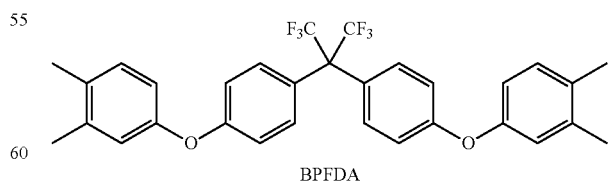
BPFDA

The present invention further includes polyamides and poly(amide-imide)s derived from the tri(benzonitrile)-diamine, in which the polyamides and poly(amide-imide)s having the general structure:

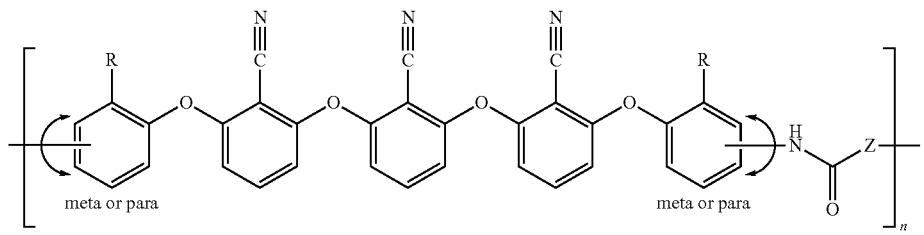

Polyamides are derived from the polymerization of the tri(benzonitrile)-diamine and an aromatic diacid or a diacid chloride, in which Z is

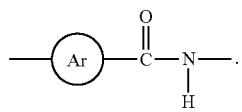

Poly(amide-imide)s are derived from the polymerization of the tri(benzonitrile)-diamine and trimellitic anhydride, trimellitic anhydride chloride, or a diacid or diacid chloride derived from trimellitic anhydride, in which Z is selected from the group consisting of:

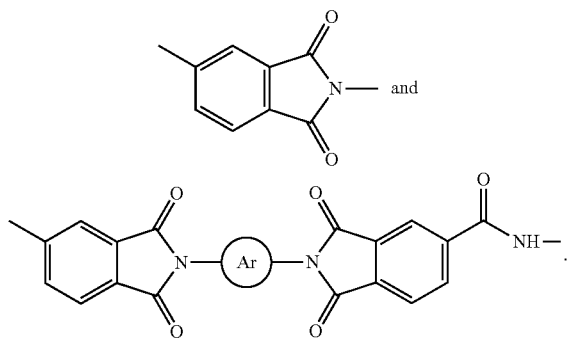

For both the polyamides and poly(amid-imide)s, Ar is selected from the group consisting of:

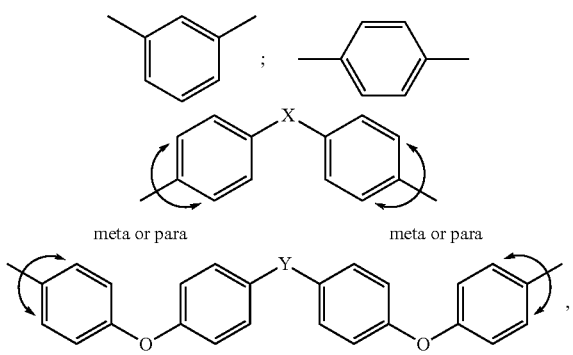

in which X and Y are selected from the group consisting of $C(CH_3)_2$, $C(CF_3)_2$, O, S, $SO_2$, and C=O.

The present invention further includes methods for synthesizing the tri(benzonitrile)-diamines. In some embodiments, a method for synthesizing a symmetrical diamine comprises the steps of: (a) demethylating 2,6-dimethoxybenzonitrile to obtain 2,6-dihydroxybenzonitrile; (b) combining the 2,6-dihydroxybenzonitrile with a fluorine-containing benzonitrile to obtain 2,6-bis(2-cyano-3-fluorophenoxy)benzonitrile; and (c) mixing the 2,6-bis(2-cyano-3-fluorophenoxy)benzonitrile with at least two molar amounts of an aminophenolate to obtain the tri(benzonitrile)-diamine.

In other embodiments, a method for synthesizing an unsymmetrical tri(benzonitrile)-diamine comprises the steps of: (a) demethylating 2,6-dimethoxybenzonitrile to obtain 2,6-dihydroxybenzonitrile; (b) combining the 2,6-dihydroxybenzonitrile with a fluorine-containing benzonitrile to obtain 2,6-bis(2-cyano-3-fluorophenoxy)benzonitrile; (c) mixing the 2,6-bis(2-cyano-3-fluorophenoxy)benzonitrile with an equimolar amount of para-aminophenolate at 80-100° C. to obtain a reaction mixture; (d) allowing the reaction mixture to cool to room temperature; and (e) adding and mixing an equimolar amount of meta-aminophenolate at 80-100° C. to obtain the unsymmetrical tri(benzonitrile)-diamine of claim 1.

The present invention further includes methods for synthesizing polymers derived from the tri(benzonitrile)-diamines. A method for synthesizing a polyimide according to the present invention comprises the steps of: (a) mixing a tri(benzonitrile)-diamine with a dianhydride in a 1:1 molar ratio in a polar solvent to generate a poly(amic acid) precursor; and (b) imidizing the poly(amic acid) precursor to obtain the polyimide.

In some embodiments, a method for synthesizing a polyamide according to the present invention comprises the step of mixing the tri(benzonitrile)-diamine and a diacid chloride in a 1:1 molar ratio in a polar solvent at low temperature to obtain the polyamide. In other embodiments, polyamides may be synthesized by a method comprising the steps of: (a) mixing the tri(benzonitrile)-diamine and a diacid in a 1:1 molar ratio in a polar solvent; (b) adding a promoter-catalyst composition comprising triphenyl phosphite (TPP) and pyridine (py) in a molar ratio of diacid:TPP:py of 1:2:2; and (c) heating to 100-120° C. to obtain the polyamide.

In some embodiments, a method for synthesizing a poly(amide-imide) according to the present invention comprises the steps of: (a) mixing the tri(benzonitrile)-diamine and an acid chloride-anhydride or a diacid chloride in a polar solvent in stoichiometric ratio at 0° C. to generate a mixture comprising an amine-anhydride AB-monomer; (b) warming the mixture to room temperature to generate a solution comprising a poly(amic acid) precursor; (c) heating the solution to 160-200° C. to generate the poly(amide-imide). In other embodiments, poly(amide-imide)s may be synthesized by a method comprising the steps of: (a) mixing the tri(benzonitrile)-diamine and an acid-anhydride or a diacid in a stoichiometric ratio in a polar solvent to form a mixture comprising diacid-di(amic acid); (b) adding to the mixture a chloride and a promoter-catalyst composition comprising triphenyl phosphite (TPP) and pyridine (py) in a molar ratio of diacid:TPP:

py having the value of 1:2:2; and (c) heating to 100-120° C. and then to 160-200° C. to sequentially form amide and imide moieties to generate the poly(amide-imide). In a further embodiment, poly(amide-imide)s may be synthesized using chemical imidization by: (a) mixing the tri(benzonitrile)-diamine and an acid-anhydride or a diacid in a stoichiometric ratio in a polar solvent to form a mixture comprising diaciddi(amic acid); (b) adding to the mixture a chloride and a promoter-catalyst composition comprising triphenyl phosphite (TPP) and pyridine (py) in a molar ratio of diacid:TPP:py having the value of 1:2:2; (c) adding acetic anhydride and triethylamine in excess; and (d) heating 100-120° C.

DETAILED DESCRIPTION OF THE INVENTION

Figure 1:
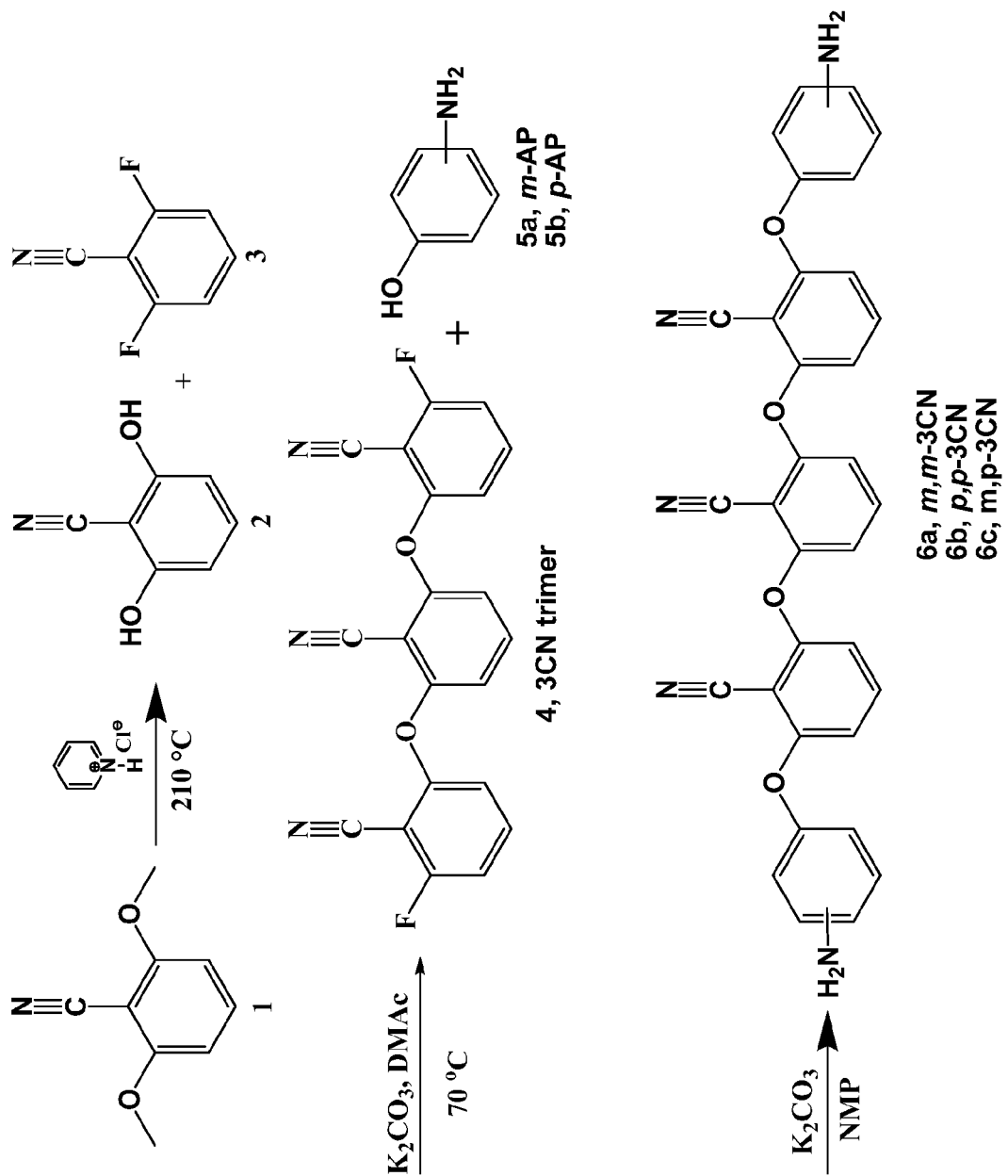
FIG. 1 illustrates an exemplary synthesis method for symmetrical and unsymmetrical diamines according to the present invention.

The present invention includes compositions and methods of preparation for diamines containing three ether-linked benzonitrile moieties and functional polymers manufactured using the disclosed diamines. For example, the presently disclosed multi(ether-benzonitrile) diamines may polymerize with: (i) a dianhydride to form a polyimide; (ii) a diacid chloride directly or with a dicarboxylic acid (diacid) in conjunction with a suitable promoter/catalyst combination such as triethylphosphite/pyridine to form a polyamide; and (iii) 1,2,4,-benzenetricarboxylic anhydride (trimellitic anhydride), trimellitic anhydride chloride, or a diacid/diacid chloride derived from trimellitic anhydride and an aromatic diamine to form a poly(amide-imide). Because of the high thermal stability and reliable film fabrication process of these polymers, they provide an excellent platform to balance the needs for high dielectric constant, low dielectric loss, and thermal stability in a variety of applications, such as high performance capacitors. Polyimides in particular have found utility in high performance films, coatings, microelectronics, optoelectronics, adhesives, aerospace structures, and liquid crystal displays.

The presently invention includes symmetrical and unsymmetrical diamines having the following general structure:

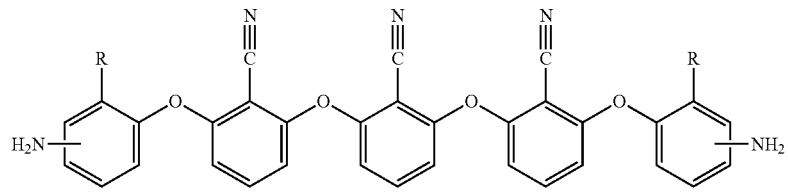

in which the substitution patterns of the two amino groups with reference to the oxygen atoms are meta or para. R is H, CH$_3$, Cl, F, or CF$_3$, and both R groups are the same. The two amino groups may have the same orientation as compared to each other i.e. meta-meta or para-para to obtain a symmetrical diamine, or they may have a different orientation to obtain an unsymmetrical diamine.

The present invention further includes methods of synthesizing diamines using a three-step process. The general method for synthesizing symmetrical diamines begins with demethylating 2,6-dimethoxybenzonitrile to obtain 2,6-dihydroxybenzonitrile. In the next step, a fluoro-endcapped multi (benzonitrile-ether)-containing intermediate (2,6-bis(2-cyano-3-fluorophenoxy)benzonitrile) is obtained by combining the 2,6-dihydroxybenzonitrile with a fluorine-containing benzonitrile such as 2,6-difluorobenzonitrile at a temperature of 65-70° C. The method concludes with the third step of replacing the two terminal fluorides or chlorides with two aminophenolates to obtain the diamine. The success of the diamine synthesis is based on the critical tactic to generate the fluoro-endcapped multi(benzonitrile-ether)-containing intermediate by exploiting the fact that only one fluoride of 2,6-difluorobenzonitrile is replaced by a phenolate nucleophile at reaction temperature around 65-70° C. and using one equivalent of 2,6-difluorobenzonitrile per phenolate nucleophile. Because aromatic chlorides are less reactive than its fluoride counterpart, 2-chloro-6-fluorobenzonitrile, for example, may alternatively be used in place of 2,6-difluorobenzonitrile.

Unsymmetrical diamines may be synthesized by the following general method. 2,6-bis(2-cyano-3-fluorophenoxy) benzonitrile, which may be synthesized as described herein, is mixed with an equimolar amount of para-aminophenolate at 80-100° C. This reaction mixture is allowed to cool to room temperature, after which an equimolar amount of meta-aminophenolate is added and mixed at 80-100° C. to obtain the unsymmetrical tri(benzonitrile)-diamine of claim 1

Referring now to the drawings, like reference numerals may designate like or corresponding parts throughout the several views. FIG. 1 illustrates an exemplary synthesis method for several diamines, 2,6-bis[3-(3-aminophenoxy)-2-cyanophenoxy]benzonitrile and 2,6-bis[3-(4-aminophenoxy)-2-cyanophenoxy]benzonitrile, and 2-[3-(4-aminophenoxy)-2-cyanophenoxy]-6-[3-(3-aminophenoxy)-2-cyanophenoxy]benzonitrile (6a, 6b, and 6c; m,m-, p,p-, and m,p-3CN, respectively) according to the present invention in which R is H. In this three-step synthetic route, 2,6-dimethoxybenzonitrile (1) is demethylated to 2,6-dihydroxybenzonitrile (2). One method utilizes boron tribromide. However, the demethylation time is long, and the reaction work-up is time-consuming. Therefore, as shown in FIG. 1, pyridine hydrochloride may be used instead. The demethylation reaction may be completed much quicker, and the purity and yield of the isolated product are comparable with the result of the boron tribromide method. The second step in the diamine synthesis also proved challenging. Nucleophilic substitution of compound 2 with 2,6-bis(2-fluoro-6-oxybenzonitrile)benzonitrile yielded no diamine product. Compound 2 was converted into 2,6-bis(t-butyldimethylsilyloxy)benzonitrile to increase the leaving group's reactivity. However, when it was treated with 2,6-difluorobenzonitrile (3), no nucleophilic reaction occurred. As shown in FIG. 1, the 3CN trimer (4) was successfully obtained by reacting compound 2 with excess 2,6-difluorobenzonitrile (3). Nucleophilic substitution of compound 4 with at least two molar amounts of 3- or 4-aminophenol (m- and p-AP; 5a, 5b) affords m, m- and p,p-3CN, respectively. The resulting diamines (6) may be useful as monomers for synthesis of a variety of polymers.

The present invention further includes polymers manufactured using diamines according to the present invention. Polymerization of the diamine and a dianhydride yields polyimides having the following general structure:

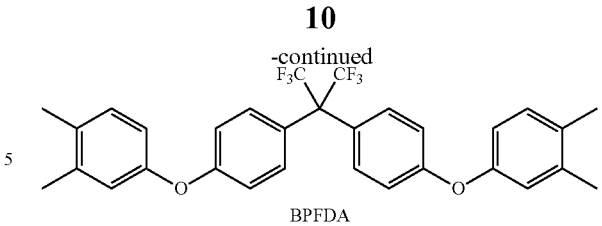

BPFDA in which R is H, CH$_3$, Cl, F, or CF$_3$ and the "meta or para" substitution pattern is with reference to the oxygen.

The present invention further includes methods of synthesizing polyimides via polymerization of the diamine and a

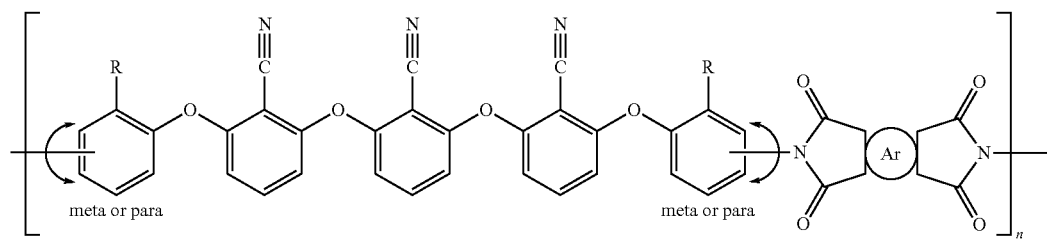

in which Ar is selected from the group consisting of:

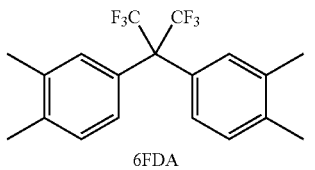

6FDA

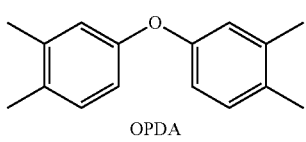

OPDA

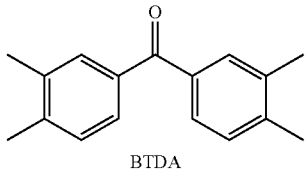

BTDA

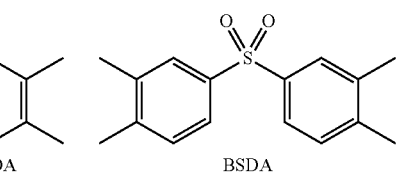

PMDA          BSDA

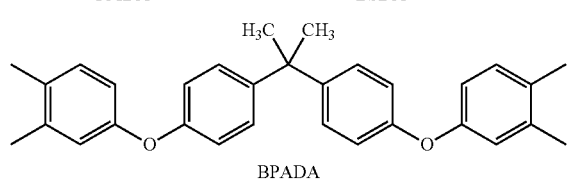

BPADA dianhydride. The synthesis of a polyimide is typically accomplished by polymerization of a diamine and a symmetrical dianhydride in a 1:1 molar ratio to generate a poly(amic acid) (PAA) precursor. The PAA precursor is then converted to the corresponding polyimide typically by either thermal curing (heating to temperatures >200° C. in solution or solid state) or chemical imidization using a dehydrating agent or promoter such as acetic anhydride/triethylamine or acetic anhydride/pyridine.

Figure 2:
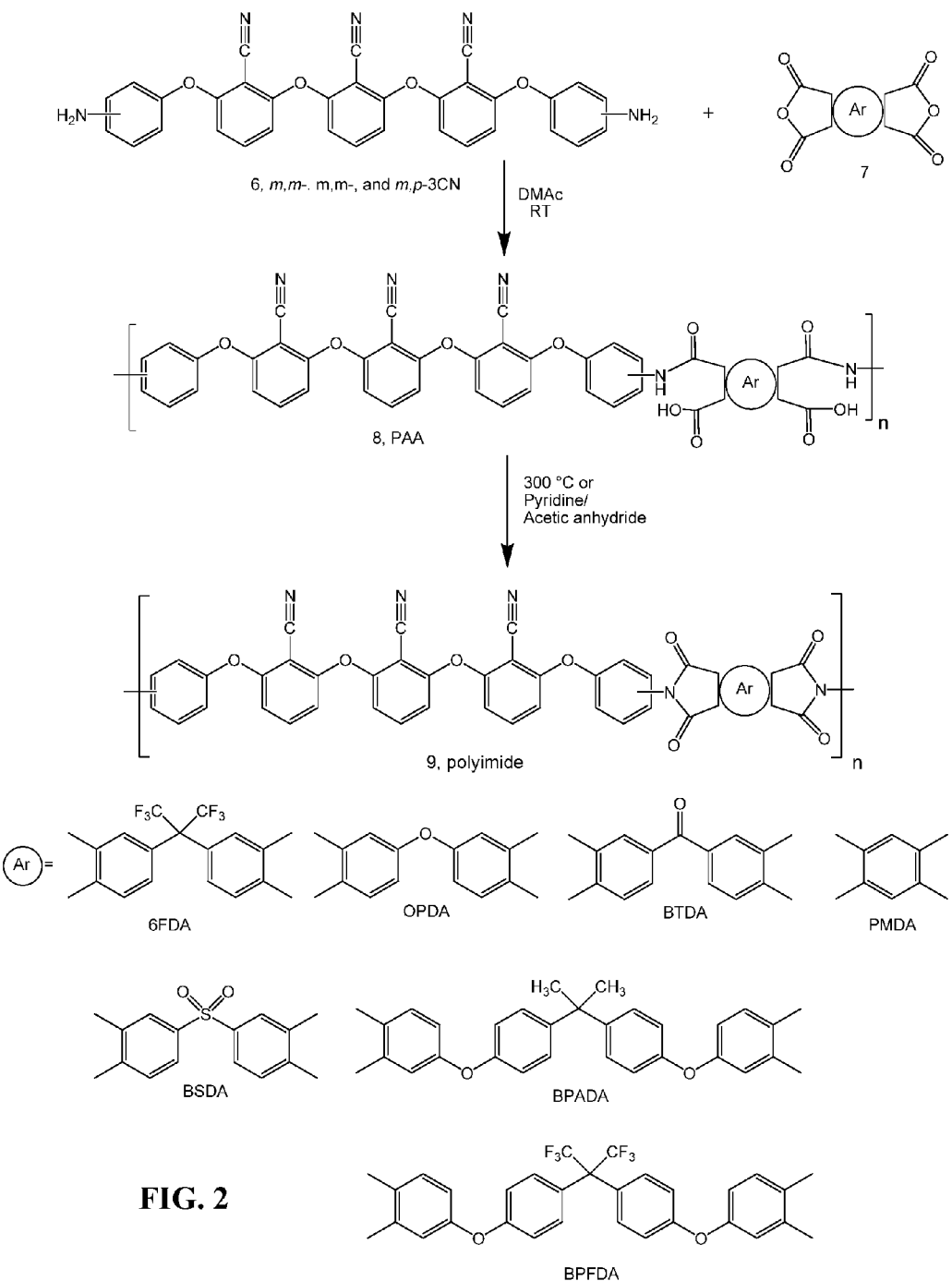
FIG. 2 illustrates an exemplary method for generating polyimides according to the present invention.

FIG. 2 illustrates an exemplary method for polymerization of the diamines (6a, 6b) as synthesized in FIG. 1 with one or more dianhydrides to form a PAA precursor (8), which are subsequently imidized by thermal or chemical methods to afford exemplary polyimides (9). The dianhydride may include 2,2'-bis-(3,4-dicarboxyphenyl) hexafluoropropane dianhydride (6FDA), 4,4'-oxydi(phthalic anhydride) (OPDA), 3,3',4,4'-benzophenone tetracarboxylic dianhydride (BTDA), pyromellitic dianhydride (PMDA), bis(3,4-dicarboxyphenoxyphenyl) sulfone dianhydride (BSDA), 5,5'-[(1-methylethylidene)bis(4,1-phenyleneoxy)]bis-1,3-isobenzofurandione (BPADA), and 5,5'-[[2,2,2-trifluoro-1-(trifluoromethyl)ethylidene]bis(4,1-phenyleneoxy)]bis-1,3-isobenzofurandione (BPFDA). Polyimide films prepared from thermal imidization are tough and creasable and may be used for the evaluation of thermal, mechanical, dielectric, and morphological properties. Their structures were verified by ATR-FTIR spectroscopy which revealed their characteristic absorptions around 2230-2232, 1777-1785 and 1714-1720 cm$^{-1}$, which are assignable to the nitrile and imide moieties, respectively (data not shown).

The present invention further includes polyamides formed by polymerization of a diamine according to the present invention with an aromatic diacid or a diacid chloride to generate the following general structure:

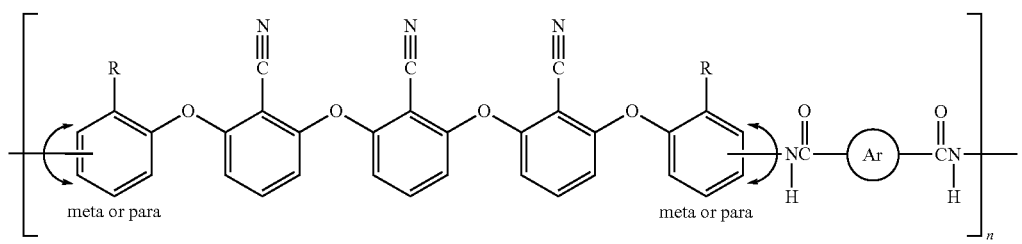

in which Ar is selected from the group consisting of:

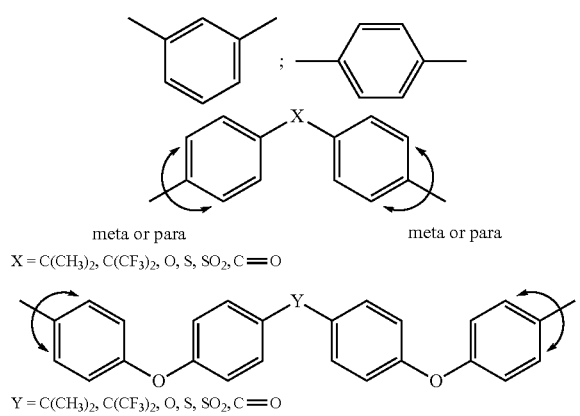

in which R is H, CH$_3$, Cl, F, or CF$_3$ and the "meta or para" substitution pattern is with reference to the oxygen.

The present invention further includes methods of synthesizing polyamides via polymerization of a diamine according to the present invention with an aromatic diacid or a diacid chloride. Synthesis of the polyamide may be accomplished by one of two general methods. The first method involves polymerization of a diamine and a diacid chloride in a 1:1 molar ratio in a suitable polar amide solvent such as N,N-dimethylformamide (DMF), N,N-dimethylacetamide (DMAc), and N-methylpyrrolidone (NMP). This method is performed at a low temperature e.g. 0° C. to room temperature (about 20-27° C.). Examples of suitable diacid chlorides include, but are not limited to, isophthaloyl dichloride or terephthaloyl dichloride. The second method of synthesizing a polyamide involves polymerization of a diamine and a dicarboxylic acid in a 1:1 molar ratio with the aid of a promoter/catalyst combination such as triphenyl phosphite(TPP)/pyridine(py) in a diacid:TPP:py molar ratio of 1:2:2 (via Yamazaki-Higashi reaction) in a suitable polar amide solvent such as DMF, DMAc, and NMP. The mixture is then heated to 100-120° C. to obtain the polyamide. Examples of suitable dicarboxylic acids include, but are not limited to, isophthalic acid and terephthalic acid.

The present invention further includes poly(amide-imide)s formed by polymerization of a diamine according to the present invention with trimellitic anhydride, trimellitic anhydride chloride, or a diacid/diacid chloride derived from trimellitic anhydride. A poly(amide-imide) generated using trimellitic anhydride has the following general structure:

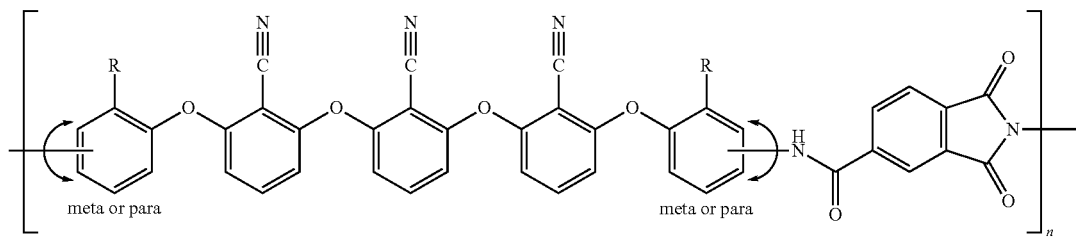

in which R is H, CH$_3$, Cl, F, or CF$_3$ and the "meta or para" substitution pattern is with reference to the oxygen.

A poly(amide-imide) generated using trimellitic anhydride chloride has the following general structure:

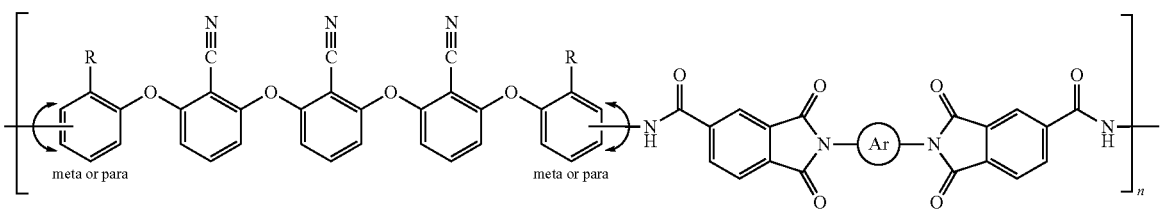

in which Ar is selected from the group consisting of:

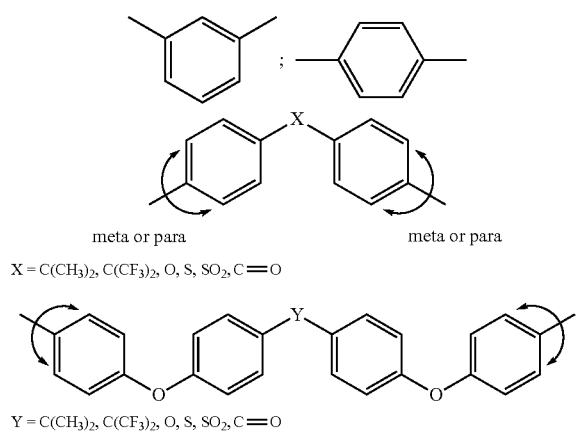

meta or para    meta or para

X = C(CH₃)₂, C(CF₃)₂, O, S, SO₂, C=O

Y = C(CH₃)₂, C(CF₃)₂, O, S, SO₂, C=O in which R is H, CH₃, Cl, F, or CF₃ and the "meta or para" substitution pattern is with reference to the oxygen.

Figure 3:
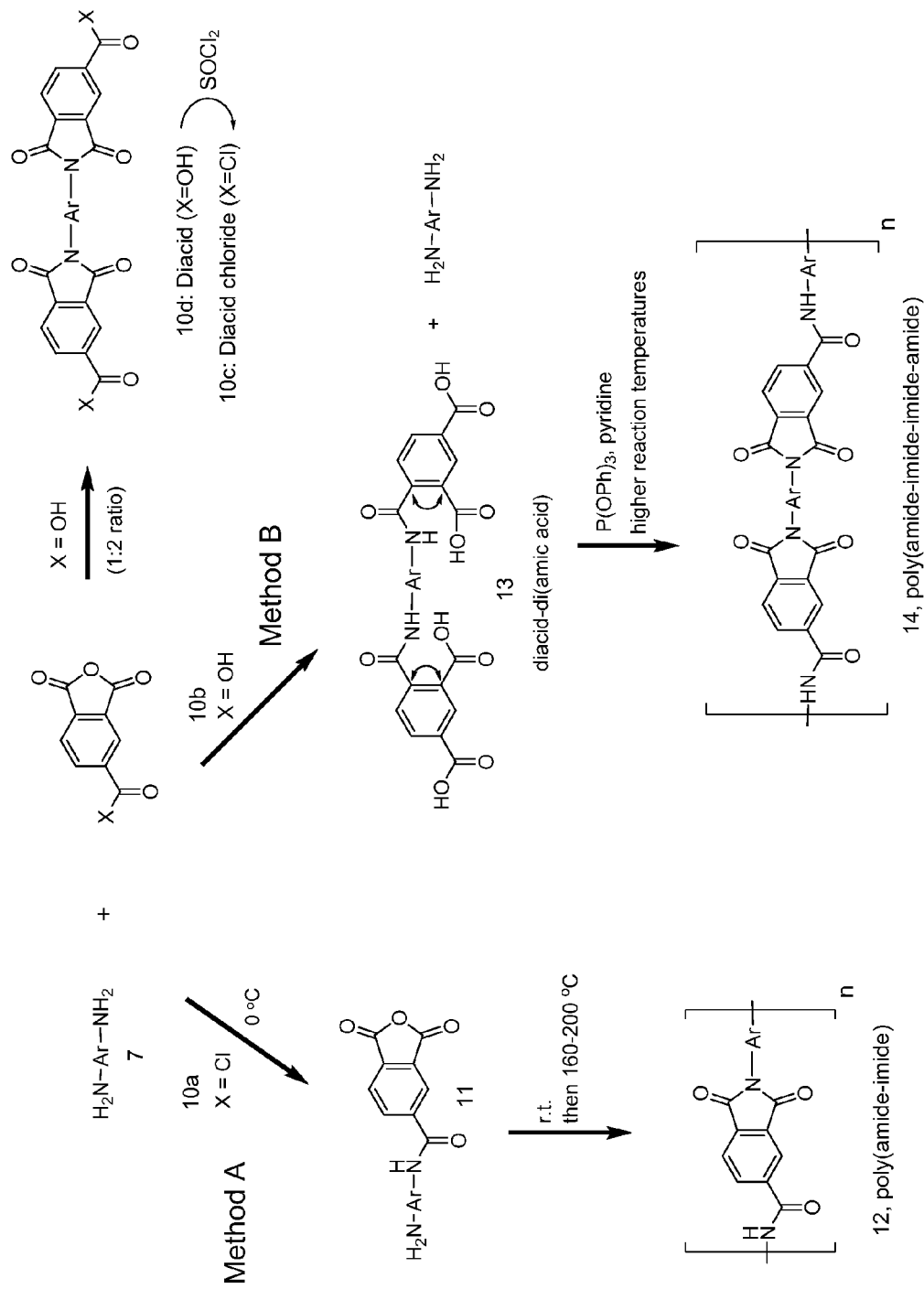
FIG. 3 illustrates exemplary methods for generating poly (amide-imide)s according to the present invention.

The present invention further includes methods of synthesizing poly(amide-imide)s via polymerization of a diamine according to the present invention with trimellitic anhydride, trimellitic anhydride chloride, or a diacid derivative generated from trimellitic anhydride. The synthesis of a poly (amide-imide) may be accomplished by one of two general methods as shown in FIG. 3. The first method (Method A) entails the polymerization of a diamine (7) and an acid chloride-anhydride or a diacid chloride (i.e. trimellitic anhydride chloride, 10a, or a diacid chloride derivative, 10c, respectively) in a stoichiometric ratio at low temperature (typically 0° C.) in a suitable polar amide solvent such as DMF, DMAc, and NMP to generate in-situ an amine-anhydride AB-monomer (11). The diacid monomer may be converted to the corresponding diacid chloride by treatment with thionyl chloride or oxalyl chloride, as shown in FIG. 3. The mixture is then warmed to room temperature to form a PAA precursor (typically not isolated). The precursor solution is heated to 160-200° C. to effect an intramolecular cyclodehydration to form the poly(amide-imide) product (12).

The second method (Method B) for synthesizing poly (amide-imide)s is based on a Yamazaki-Higashi phosphorylation reaction that entails the polymerization of a diamine and an acid-anhydride or a diacid (i.e. trimellitic anhydride, 10b, or a diacid derivative, 10d, respectively) in a stoichiometric ratio in a suitable polar amide solvent such as DMF, DMAc, and NMP to form a diacid-di(amic acid) (13). The polymerization process requires a promoter/catalyst combination such as triphenyl phosphite(TPP)/pyridine(py) in a diacid:TPP:py molar ratio of 1:2:2 and a chloride such as lithium chloride or calcium chloride (10-12%, w/v, in which v is total liquid volume) to increase to solubility of the growing polymer. The mixture is then heated to 100-120° C. and then 160-200° C. to sequentially effect polyamide formation and cyclodehydration of (amic acid) moieties to imide in the same pot to form a poly(amide-imide-imide-amide) product (14). Method B may alternatively be performed using chemical imidization. Following addition of the promoter-catalyst combination, acetic anhydride and triethylamine are added in excess. The mixture is then heated to 100-120° C. to effect amide and imide formation at a lower temperature.

The following examples and methods are presented as illustrative of the present invention or methods of carrying out the invention, and are not restrictive or limiting of the scope of the invention in any manner.

Example 1

Synthesis of 2,6-Dihydroxybenzonitrile (2-Cyanoresorcinol)

One potential method utilizes boron tribromide to demethylate 2,6-dimethoxybenzonitrile (1 in FIG. 1) to generate 2,6-dihydroxybenzonitrile (2). Into a 250 mL 3-neck round bottom flask equipped with stir bar, nitrogen inlet, thermometer, and addition funnel was charged 2,6-dimethoxybenzonitrile (3.99 g, 24.5 mmol) and methylene chloride (27 mL). The solution was cooled to −78° C. by submerging the flask in a dry ice/acetone bath. A solution of boron tribromide (25 g, 99.8 mmol) in methylene chloride (27 mL) was added dropwise via the addition funnel over a period of 1 hour. The temperature was maintained at −78° C. for 2 hours. The mixture was allowed to rise to room temperature. The reaction was then stirred at room temperature overnight and refluxed at 55° C. for 10 hours. Excess boron tribromide was decomposed carefully by the addition of moist methylene chloride. Upon removal of the solvent, the crude product was passed through a column of silica gel using 5% acetone in methylene chloride as eluent to afford 1.42 g (43.0%) of a light brown solid, m.p. 197.5-199.6° C. ¹H-NMR (DMSO-d₆): 6.39-6.41 (d, 2H, Ar—H), 7.20-7.24 (t, 1H), 10.78 (s, 2H, Ar—O—H).

Another potential method utilizes pyridine hydrochloride in place of the boron tribromide. Into a 500 mL 3-neck round bottom flask equipped with stir bar, nitrogen inlet and condenser was charged 2,6-dimethoxybenzonitrile (15.0 g, 91.9 mmol), followed by pyridine hydrochloride (150 g). The mixture was heated to 210° C. for 2 hours and allowed to cool to room temperature. Water was then added to the flask to dissolve the solidified mixture. The aqueous layer was then extracted with ethyl acetate (150 mL) 3 times. The combined organic layer was dried under anhydrous sodium sulfate, and the solvent was removed to yield 7.44 g (60.0%) of a light pink solid, m.p.: 202.8-204.8° C. ¹H-NMR (DMSO-d₆): 6.39-6.41 (d, 2H, Ar—H), 7.20-7.24 (t, 1H), 10.78 (s, 2H, Ar—O—H).

Example 2

Synthesis of 2,6-bis(2-cyano-3-fluorophenoxy)benzonitrile

Into a 500 mL 3-neck round bottom flask equipped with stir bar, condenser, nitrogen inlet, and addition funnel was charged, 2,6-difluorobenzonitrile (50.0 g, 35.9 mmol), potassium carbonate (29.80 g, 28.8 mmol), and N,N-dimethylacetamide (DMAc, 100 mL). A solution containing 2,6-dihydroxybenzonitrile (12.2 g, 9.00 mmol) and DMAc (75 mL) was added dropwise over 6 hours at 70° C. The mixture was stirred at 70° C. for 72 hours. The reaction mixture was then poured into 2 M HCl (600 mL), and the precipitate was collected by filtration and washed with water. After air drying, the solid was dissolved with acetone (600 mL). The mixture was stirred at room temperature for 3 hours, followed by filtration to remove insoluble impurities. The filtrate was evaporated to dryness on a rotary evaporator. The resulting solid was extracted with hot toluene to afford 21.48 g (64.0%) of a brown solid (3CN trimer; 4 in FIG. 1), m.p. 216.1-218.4°

C. ¹H-NMR (DMSO-$d_6$): 7.18-7.22 (m, 4H, Ar—H), 7.41-7.45 (t, 2H, Ar—H), 7.78-7.86 (m, 3H, Ar—H). ¹³C-NMR (DMSO-$d_6$): 93.61, 93.80, 97.30, 110.58, 111.48, 112.40, 112.79, 114.86, 115.40, 136.77, 136.94, 137.04, 157.41157.76, 161.88, 164.44.

Example 3

Synthesis of 2,6-bis[3-(3-aminophenoxy)-2-cyanophenoxy]benzonitrile

Into a 100 mL round bottom flask equipped with stir bar, condenser, and nitrogen inlet was charged 2,6-bis(2-cyano-3-fluorophenoxy)benzonitrile (2.21 g, 5.9 mmol), 3-aminophenol (1.41 g, 12.9 mmol), potassium carbonate (1.96 g, 14.2 mmol), and N-methyl-1-pyrrolidone (NMP, 35 mL). The mixture was stirred at 100° C. for 24 hours until GC/MS showed no remaining reactant. It was filtered, and filtrate was then poured into about 500 mL of saturated NaCl aqueous solution, followed by extraction with ethyl acetate (3×200 mL). The organic layer was combined and washed with distilled water (3×200 mL). It was then dried over sodium sulfate and filtered. Carbon black was added to the solution, which was then stirred at 65° C. for 30 minutes. The solution was passed through a Celite filter to remove carbon, and the solvent was removed using a rotary evaporator. A small amount of NMP residue in the product was removed by refluxing it in ethanol (75 mL). Product was collected by filtration and dried overnight at 80° C. in a vacuum oven to afford 2.07 g (63.3%) of a beige solid (m,m-3CN, 6a in FIG. 1), m.p. 226.3-228.9° C. ¹H-NMR (DMSO-$d_6$): 5.39 (s, 4H, $NH_2$), 6.29-6.31 (dd, 2H, Ar—H), 6.35-6.36 (m, 2H, Ar—H), 6.46-6.49 (dd, 2H, Ar—H), 6.79-6.81 (d, 2H, Ar—H), 6.97-6.99 (d, 2H, Ar—H), 7.08-7.11 (t, 2H, Ar—H), 7.20-7.21 (d, 2H, Ar—H), 7.63-7.68 (t, 2H, Ar—H), 7.80-7.83 (t, 1H, Ar—H). ¹³C-NMR (DMSO-$d_6$): 95.30, 96.92, 104.62, 106.45, 111.10, 111.84, 113.03, 114.98, 130.49, 136.17, 136.72, 150.92, 155.35, 157.70, 158.06, 160.93. Elemental analysis: Calcd.: C, 71.86; H, 3.84; N, 12.70. Found: C, 71.04; H, 3.85; N, 12.43.

Example 4

Synthesis of 2,6-bis[3-(4-aminophenoxy)-2-cyanophenoxy]benzonitrile 2,6-bis[3-(4-aminophenoxy)-2-cyanophenoxy]benzonitrile (p,p-3CN; 6b in FIG. 1) was prepared from 2,6-bis(2-cyano-3-fluorophenoxy)benzonitrile (2.00 g, 5.4 mmol), 4-aminophenol (1.29 g, 11.8 mmol), potassium carbonate (1.78 g, 12.9 mmol), and NMP (32 mL) using the same procedure as Example 3 to obtain 1.52 g (51.5%) of beige solid, m.p. 242.6-243.8° C. (dec.). ¹H-NMR (DMSO-$d_6$): 5.18 (s, 4H, Ar—H), 6.57-6.65 (m, 6H, Ar—H), 6.88-6.92 (m, 2H, Ar—H), 7.58-7.61 (t, 2H, Ar—H), 7.77-7.80 (t, 1H, Ar—H). Elemental analysis: Calcd.: C, 71.86; H, 3.84; N, 12.70. Found: C, 71.40; H, 4.00; N, 12.33.

Example 5

Synthesis of 2-[3-(4-aminophenoxy)-2-cyanophenoxy]-6-[3-(3-aminophenoxy)-2-cyanophenoxy]benzonitrile Into a 250 mL round bottom flask equipped with stir bar, condenser and nitrogen inlet was charged 2,6-bis(2-cyano-3-fluorophenoxy)benzonitrile (8.00 g, 21.4 mmol), 4-aminophenol (2.34 g, 21.4 mmol), potassium carbonate (3.56 g, 25.8 mmol) and N-methyl-1-pyrrolidone (NMP, 140 mL). The mixture was stirred at 100° C. for 24 hours until GC/MS showed no remaining reactant. It was allowed to cool to room temperature, followed by the addition of 3-aminophenol (2.34 g, 21.4 mmol) and potassium carbonate (3.56 g, 25.8 mmol). The mixture was stirred at 100° C. for 24 hours until GC/MS showed no remaining reactant. It was filtered and then the filtrate was poured into about 500 mL of saturated NaCl aqueous solution, followed by extraction with ethyl acetate (3×500 mL). The organic layer was combined and washed with distilled water (3×500 mL). It was then dried over sodium sulfate and filtered. Carbon black was added to the solution, which was then stirred at 65° C. for 30 minutes. It was passed through a Celite filter to remove carbon, and the solvent was removed by a rotary evaporator. A small amount of NMP residue in the product was removed by refluxing it in ethanol (75 mL). Product was collected by filtration and dried overnight at 80° C. in a vacuum oven to afford 5.73 g (48.5%) of a beige solid, m.p. 196.2-197.8° C. ¹H-NMR (DMSO-$d_6$): 5.16 (s, 2H, Ar—H), 5.37 (s, 2H, Ar—H), 6.29-6.31 (dd, 1H, Ar—H), 6.34-6.35 (t, 1H, Ar—H), 6.46-6.47 (dd, 1H, Ar—H), 6.60-6.65 (m, 3H, Ar—H), 6.78-6.80 (d, 1H, Ar—H), 6.88-6.93 (t, 3H, Ar—H), 6.96-6.98 (d, 1H, Ar—H), 7.07-7.15 (m, 3H, Ar—H), 7.58-7.62 (t, 1H, Ar—H), 7.64-7.68 (t, 1H, Ar—H), 7.78-7.80 (t, 1H, Ar—H). Elemental analysis: Calcd: C, 71.86; H, 3.84; N, 12.70. Found: C, 71.50; H, 3.87; N, 12.64.

Example 6

General Procedure for Polyimide Synthesis

Into a 50 mL round bottom flask equipped with stir bar and nitrogen inlet was charged 2,6-bis[3-(3-aminophenoxy)-2-cyanophenoxy]benzonitrile according to Example 3 and DMAc (8.00 g). After the 2,6-bis[3-(3-aminophenoxy)-2-cyanophenoxy]benzonitrile was dissolved, 6FDA (0.8055 g, 1.81 mmol) was added and the mixture was stirred for 24 hours to form a solution containing a PAA precursor (8). The solution became increasingly viscous as the reaction proceeded.

In one method, the PAA solution may be undergo thermal imidization to produce the polyimide (9 in FIG. 2). The viscous PAA solution was poured onto six different 2 inch×2 inch glass plates (2×0.33 g of solution, 2×0.88 g, and 2×1.76 g). The plates were manipulated by tilting until the entire surface was covered by solution. Once completed, all plates were placed in a vacuum oven which was maintained at 50° C. and reduced pressure overnight. The oven pressure was released under nitrogen, and the temperature ramped to a final temperature of 300° C. at hourly intervals (100° C., 150° C. 175° C. 200° C., 250° C., 300° C.). The coated plates were allowed to cool, and the polyimide films were removed from the plates by submerging them in water overnight. The resulting films were tough, creasable, and transparent.

In another method, the PAA solution may undergo chemical imidization. 1 mL each of triethylamine (or pyridine) and acetic anhydride were added to the remaining PAA solution. The mixture was stirred for 24 hours, followed by precipitation into ethanol. Fibrous polyimide was collected by filtration and Soxhlet extracted with ethanol for 48 hours. The polyimide was then dried overnight in a vacuum oven at 100° C.

Example 7

Thermal and Mechanical Properties of Polyimides

Table 1 shows the results of thermal and mechanical analysis of polyimides fabricated according to the present invention using thermal imidization. The glass transition temperature ($T_g$) of each polyimide was determined using a dynamic mechanical analysis (DMA) instrument and was measured from the peak of tan δ as an average value taken from four measurements. The modulus (E) was determined in tension at 25° C. as an average value taken from five specimens per polyimide. Thermogravimetric analysis was conducted at a heating rate of 10° C./min.

TABLE 1

Thermal and Mechanical Properties of Polyimides

| Diamine | Dianhydride | $T_g{}^a$ (DMA, ° C.) | $E^b$ (GPa) | $T_{d5\%}$ in air$^c$ (° C.) | $T_{d5\%}$ in $N_2{}^c$ (° C.) |
|---|---|---|---|---|---|
| m,m-3CN | 6FDA | 226 | 1.95 ± 0.22 | 503 | 487 |
| m,m-3CN | OPDA | 216 | 1.63 ± 0.17 | 501 | 476 |
| m,m-3CN | BTDA | 218 | 2.28 ± 0.31 | 502 | 482 |
| m,m-3CN | PMDA | 305 | 2.60 ± 0.27 | 493 | 469 |
| p,m-3CN | 6FDA | 232 | 2.10 ± 0.15 | 504 | 484 |
| p,m-3CN | OPDA | 229 | 1.71 ± 0.27 | 502 | 492 |
| p,p-3CN | OPDA | 235 | 1.85 ± 0.29 | 496 | 463 |
| p,p-3CN | 6FDA | 244 | 2.28 ± 0.19 | 499 | 484 |
| p,p-3CN | BTDA | 238 | 2.47 ± 0.15 | 502 | 487 |
| p,p-3CN | PMDA | 341 | 2.86 ± 0.24 | 497 | 473 |

As shown in Table 1, the polymer rigidity imposes a direct effect on the $T_g$ observed. Polyimides prepared from an m,m-3CN diamine show a lower $T_g$ than those derived from a p,p-3CN diamine. Nevertheless, all of the polyimides demonstrate a high $T_g$ in the range of 216 to 341° C. The polyimide films are strong and tough with a tensile modulus of 1.95-2.86 GPa. Table 1 also gives the temperature of the 5 wt % gravimetric loss ($T_{d5}\%$) in nitrogen and in air, with weight losses ranging from 493-503° C. and 469-487° C. in air and nitrogen, respectively. Interestingly, all of the polymers have slightly higher degradation temperatures (~20° C.) in air than in nitrogen.

Example 8

Dielectric Properties of Polyimides

To evaluate the suitability of the polyimide films for use in high temperature and high energy density capacitors, the dielectric properties of the films were determined using broadband dielectric spectroscopy (BDS) and displacement-electric field (D-E) loop measurements. The BDS measurements of the γ transition reveal how much dipole switching contributes to the dielectric constant. It is worth noting that dipole switching only becomes active at and above the γ transition temperature. The purpose of the D-E loop measurements was to investigate the high field performance of the polyimide film and measure the dielectric constant at high field strengths, as well as to estimate how lossy the material is based on the hysteresis and determine the breakdown strength.

The samples made according to the present invention using thermal imidization were dried in a vacuum oven for 24 hours at 130° C. To improve electrical contact, 38 μm thick sample films were coated with a thin layer (200 nm) of aluminum or silver on both sides by physical vapor deposition prior to measurements and kept in a desiccator filled with Drierite. The BDS measurements are carried out on the silver-coated sample films using a Novocontrol Concept 80 broadband dielectric spectrometer. The temperature of the sample was programmed to linearly change from −150 to 190° C. at a rate of 2° C./min. The BDS spectrometer applied a set of sinusoidal voltages of 1 V r.m.s. from 107 Hz to 1 Hz across a sample film every 14 seconds during the temperature ramping and recorded the resulting current.

Figure 4:
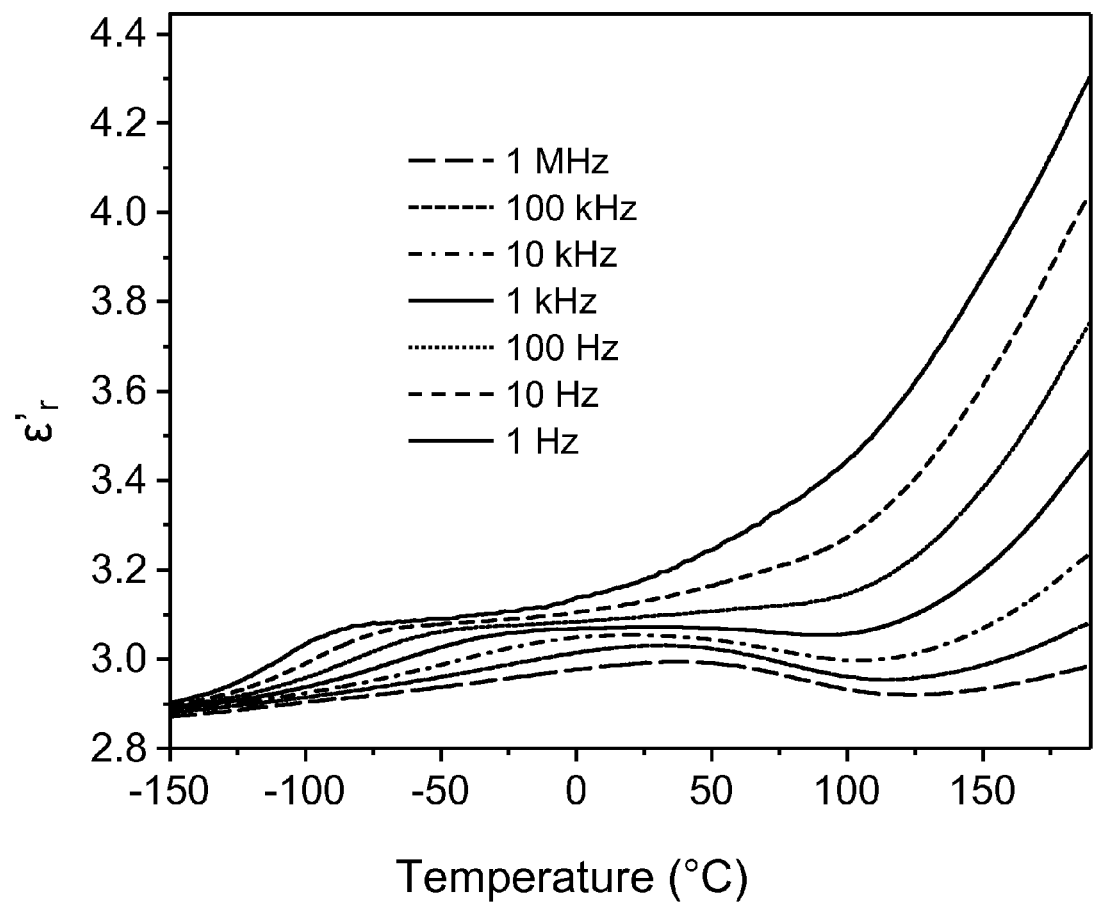
FIG. 4 is a plot of the dielectric constant $\in_r'$ of the m,m-3CN-OPDA aluminum-coated sample with respect to temperature.

FIG. 4 is a plot of the dielectric constant $\in_r'$ of the m,m-3CN-OPDA aluminum-coated sample with respect to temperature. The $\in_r'$ decreases with increasing frequency because of dielectric dispersion (dipole motion lags behind the applied electric field). There is a γ transition ($\in_r'$ increases by 0.19) occurring at about −125° C. for the 1 Hz frequency. This γ transition shifts to a higher temperature as the frequency is increased, which can be explained with dipole switching at a higher frequency at higher temperatures. The $\in_r'$ from the BDS measurements at the low field (about 18 kV/m) is on average 3.0.

Figure 5:
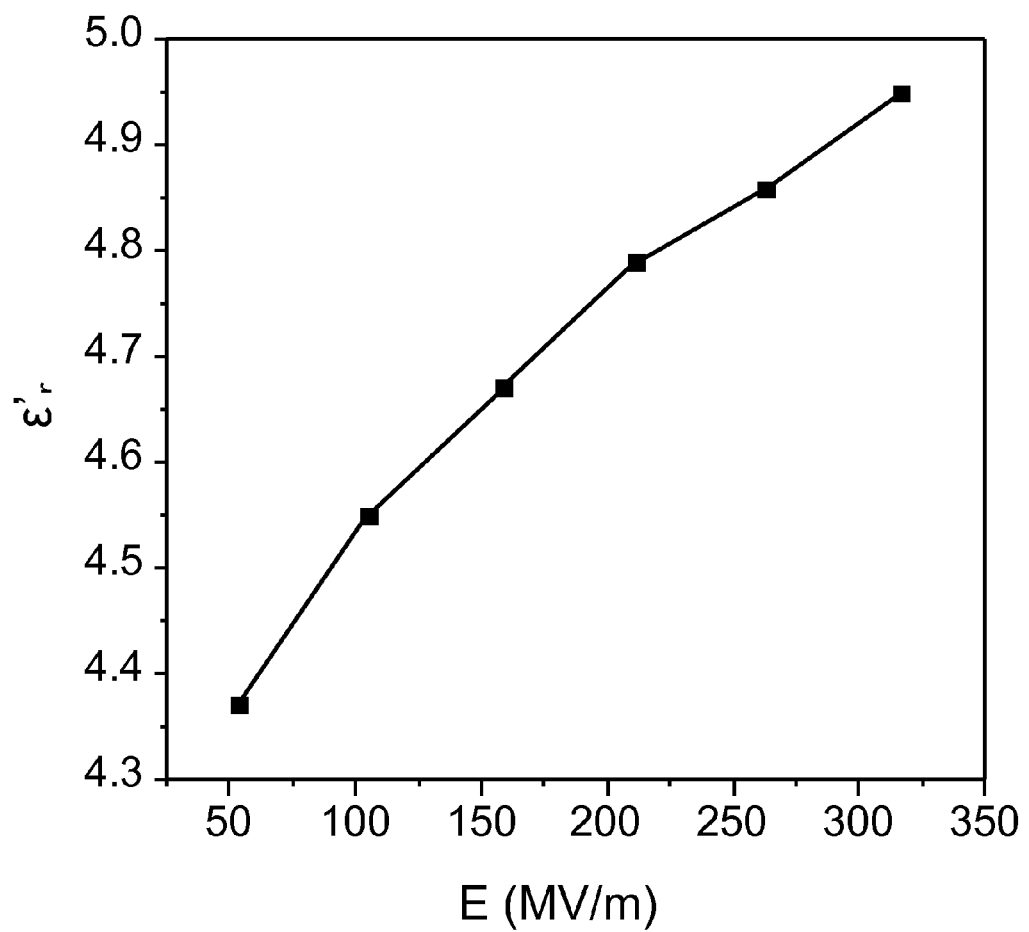
FIG. 5 is a plot of the $\in_r'$ of the m,m-3CN-OPDA silver-coated sample with respect to E (MV/m).

The silver-coated sample films were used in the D-E loop measurements performed at 23° C., 100° C., and 190° C. Samples of additional polyimides (LaRC™-CP2, Kapton®, and ULTEM®) were included for comparison. The D-E loops were measured with a Precision Premium II ferroelectric analyzer (Radiant Technologies) by applying two consecutive sine waves with equal amplitudes to the sample. The frequency of each wave was 10 Hz. The peak amplitude of the voltage was increased every two cycles starting at a field strength of 50 MV/m up to 316 MV/m. The results of the dielectric measurements are summarized in Table 2, in which the permittivities are calculated from slopes of D-E loops. The data for 23° C. and 100° C. are from loops run at 10 Hz and data for 190° C. is from loops run at 1000 Hz. 1000 Hz was used to avoid contribution of ionic conduction to the slope at high temperatures. FIG. 5 is a plot of the $\in_r'$ of the m,m-3CN-OPDA silver-coated sample with respect to E (MV/m). The $\in_r'$, which is calculated from the D-E loops (hundreds of MV/m), is on average 4.7 and increases with increasing field strength.

TABLE 2

Permittivities of Polyimides

| Sample ID | $T_g$ (DMA, ° C.) | 23° C., 100 Hz | 100° C., 100 Hz | 190° C., 1 kHz |
|---|---|---|---|---|
| m,m-3CN-BTDA | 218 | 4.0 | 4.3 | 4.3 |
| m,m-3CN-6FDA | 226 | 3.7 | 3.7 | 4.1 |
| m,m-3CN-OPDA | 216 | 4.0 | 4.2 | 4.5 |
| m,m-3CN -PMDA | 305 | 3.8 | 4.8 | 4.6 |
| p,p-3CN-6FDA | 244 | 4.3 | 4.5 | 4.9 |
| p,p-3CN-BTDA | 238 | 3.9 | 4.0 | 4.3 |
| p,p-3CN-OPDA | 232 | 4.0 | 4.1 | 4.5 |
| p,p-3CN-PMDA | 341 | 3.7 | 4.3 | 4.6 |
| p,m-3CN-6FDA | 229 | 4.1 | 5.2 | 4.6 |
| p,m-3CN-OPDA | 220 | 4.0 | 4.1 | 4.3 |
| 3,4-APBN-OPDA | 255 | 4.2 | 4.5 | 4.7 |
| 3,3-APBN-OPDA | 255 | 3.8 | 4.0 | 4.0 |
| LaRC ™-CP2 | 219 | 3.4 | 3.1 | 2.9 |
| Kapton ® | >360 | 3.2 | 3.2 | 3.1 |
| ULTEM ® | 217 | 3.6 | 3.4 | 3.0 |

Due to their high dielectric constant and low dielectric loss, the presently disclosed functional polymers are particularly useful for capacitor applications, especially those applications requiring thermal stability. The 2,6-linkage of the phenyl rings in the diamine backbone restricts flipping of the phenyl rings and deters the randomization of aligned dipoles (as compared to 2,5-linkage) at high temperatures, which helps to provide the dipole alignment stability necessary to achieve the desired properties for electrical energy storage. In particular, polyimides according to the present invention demonstrate a high-K, low dissipation factor, high thermal stability, simple processability, and good dielectric properties over a broad frequency range.

Although specific exemplary embodiments have been described in detail in the foregoing description and illustrated in the drawings, various other embodiments, changes, and modifications to the disclosed embodiment(s) will become apparent to those skilled in the art. All such other embodiments, changes, and modifications are intended to come within the spirit and scope of the appended claims.

What is claimed is:

1. A tri(benzonitrile)-diamine having a general structure:

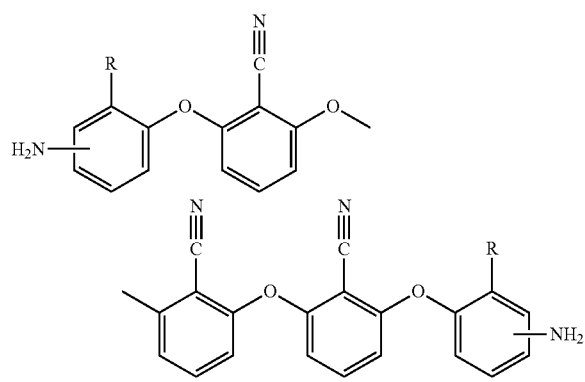

wherein $NH_2$ is meta or para with reference to oxygen and wherein R is selected from the group consisting of H, $CH_3$, Cl, F, and $CF_3$.

2. A polyimide derived from the tri(benzonitrile)-diamine of claim 1 and a dianhydride, the polyimide having the general structure:

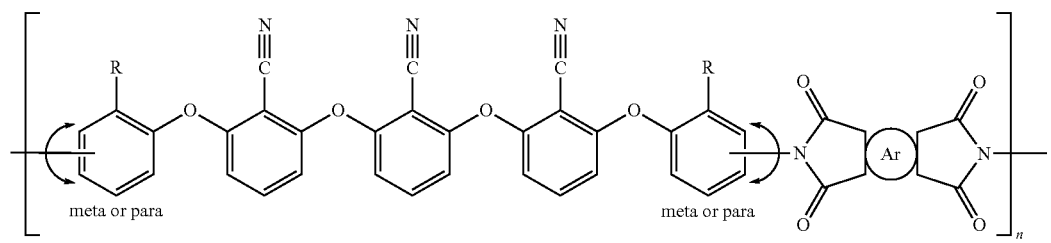

Ar is selected from the group consisting of:

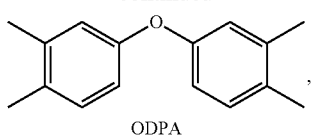
ODPA

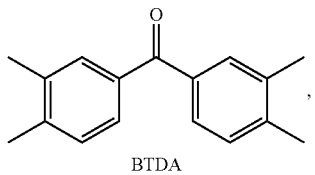
BTDA

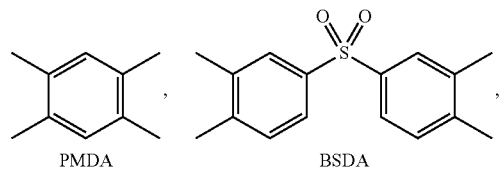
PMDA          BSDA

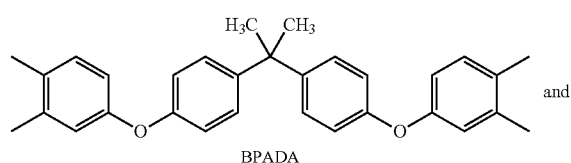
BPADA
and

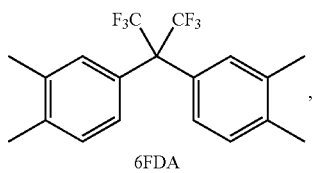
6FDA

BPFDA

3. Polyamides and poly(amide-imide)s derived from the tri(benzonitrile)-diamine of claim 1 having the general structure:

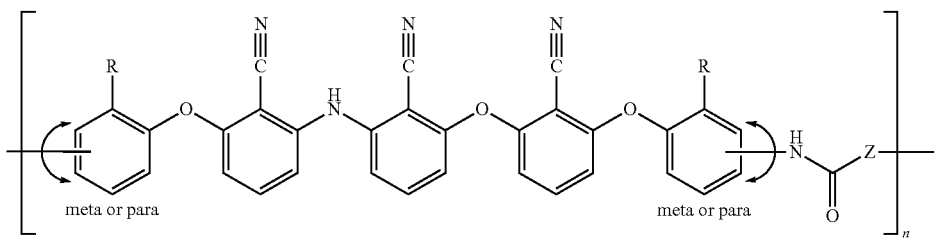

wherein the polyamide is derived from the tri(benzonitrile)-diamine of claim 1 and an aromatic diacid or a diacid chloride, wherein Z is

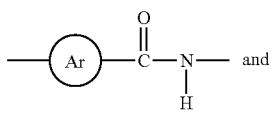   and wherein the poly(amide-imide) is derived from the tri(benzonitrile)-diamine of claim 1 and trimellitic anhydride, trimellitic anhydride chloride, or a diacid or diacid chloride derived from trimellitic anhydride, wherein Z is selected from the group consisting of:

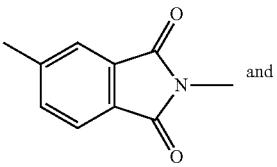   and

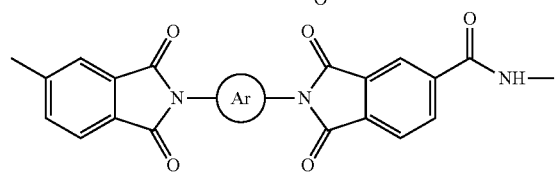

Ar being selected from the group consisting of:

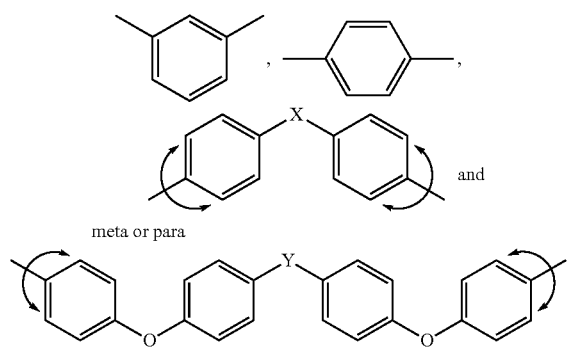

wherein X and Y are selected from the group consisting of $C(CH_3)_2$, $C(CF_3)_2$, O, S, $SO_2$, and C=O.

4. A method for synthesizing a symmetrical tri(benzonitrile)-diamine according to claim 1 comprising the steps of:
   a. demethylating 2,6-dimethoxybenzonitrile to obtain 2,6-dihydroxybenzonitrile;
   b. combining the 2,6-dihydroxybenzonitrile with a fluorine-containing benzonitrile to obtain 2,6-bis(2-cyano-3-fluorophenoxy)benzonitrile; and
   c. mixing the 2,6-bis(2-cyano-3-fluorophenoxy)benzonitrile with at least two molar amounts of an aminophenolate to obtain the symmetrical tri(benzonitrile)-diamine of claim 1.

5. A method for synthesizing an unsymmetrical tri(benzonitrile)-diamine according to claim 1 comprising the steps of:
   a. demethylating 2,6-dimethoxybenzonitrile to obtain 2,6-dihydroxybenzonitrile;
   b. combining the 2,6-dihydroxybenzonitrile with a fluorine-containing benzonitrile to obtain 2,6-bis(2-cyano-3-fluorophenoxy)benzonitrile;
   c. mixing the 2,6-bis(2-cyano-3-fluorophenoxy)benzonitrile with an equimolar amount of para-aminophenolate at 80-100° C. to obtain a reaction mixture;
   d. allowing the reaction mixture to cool to room temperature; and
   e. adding and mixing an equimolar amount of meta-aminophenolate at 80-100° C. to obtain the unsymmetrical tri(benzonitrile)-diamine of claim 1.

6. The method of claim 4 wherein the tri(benzonitrile)-diamine is selected from the group consisting of 2,6-bis[3-(3-aminophenoxy)-2-cyanophenoxy]b enzonitrile and 2,6-bis[3-(4-aminophenoxy)-2-cyanophenoxy]benzonitrile.

7. A method for synthesizing the polyimide of claim 2 comprising the steps of:
   a. mixing a tri(benzonitrile)-diamine according to claim 1 with a dianhydride in a 1:1 molar ratio in a polar solvent to generate a poly(amic acid) precursor; and
   b. imidizing the poly(amic acid) precursor to obtain the polyimide of claim 2.

8. The method of claim 7 wherein the dianhydride is selected from the group consisting of 2,2'-bis-(3,4-dicarboxyphenyl)hexafluoropropane dianhydride, 4,4'-oxydi(phthalic anhydride), 3,3',4,4'-benzophenone tetracarboxylic dianhydride, pyromellitic dianhydride, bis(3,4-dicarboxyphenoxyphenyl) sulfone dianhydride, 5,5'-[(1-methylethylidene)bis(4,1-phenyleneoxy)]bis-1,3-isobenzofurandione, and 5,5'-[[2,2,2-trifluoro-1-(trifluoromethyl)ethylidene]bis(4,1-phenyleneoxy)]bis-1,3-isobenzofurandione.

9. The method of claim 7 wherein the step of imidizing the poly(amic acid) precursor comprises thermal curing.

10. The method of claim 7 wherein the step of imidizing the poly(amic acid) precursor comprises chemical imidization using at least one of a dehydrating agent and a promoter.

11. A method for synthesizing a polyamide according to claim 3 comprising the step of mixing the tri(benzonitrile)-diamine of claim 1 and a diacid chloride in a 1:1 molar ratio in a polar solvent at low temperature to obtain the polyamide.

12. A method for synthesizing a polyamide according to claim 3 comprising the steps of:

a. mixing the tri(benzonitrile)-diamine of claim 1 and a diacid in a 1:1 molar ratio in a polar solvent;

b. adding a promoter-catalyst composition comprising triphenyl phosphite (TPP) and pyridine (py) in a molar ratio of diacid:TPP:py of 1:2:2; and c. heating to 100-120° C. to obtain the polyamide.

13. A method for synthesizing a poly(amide-imide) according to claim 3 comprising the steps of:

a. mixing the tri(benzonitrile)-diamine of claim 1 and an acid chloride-anhydride or a diacid chloride in a polar solvent in stoichiometric ratio at 0° C. to generate a mixture comprising an amine-anhydride AB-monomer;

b. warming the mixture to room temperature to generate a solution comprising poly(amic acid) precursor; and c. heating the solution to 160-200° C. to generate the poly(amide-imide).

14. A method for synthesizing a poly(amide-imide) according to claim 3 comprising the steps of:

a. mixing the tri(benzonitrile)-diamine of claim 1 and an acid-anhydride or a diacid in a stoichiometric ratio in a polar solvent to form a mixture comprising diacid-di(amic acid);

b. adding a chloride and a promoter-catalyst composition to the mixture, wherein the promoter-catalyst composition comprises triphenyl phosphite (TPP) and pyridine (py) in a molar ratio of 1 (diacid): 2 (TPP): 2 (py); and c. heating the mixture to 100-120° C. and then 160-200° C. to sequentially form amide and imide moieties to generate the poly(amide-imide).

15. A method for synthesizing a poly(amide-imide) according to claim 3 comprising the steps of:

a. mixing the tri(benzonitrile)-diamine of claim 1 and an acid-anhydride or a diacid in a stoichiometric ratio in a polar solvent to form a mixture comprising diacid-di(amic acid);

b. adding a chloride and a promoter-catalyst composition to the mixture, wherein the promoter-catalyst composition comprises triphenyl phosphite (TPP) and pyridine (py) in a molar ratio of 1 (diacid): 2 (TPP): 2 (py);

c. adding acetic anhydride and triethylamine in excess; and d. heating the mixture to 100-120° C. to generate the poly(amide-imide).

* * * * *